United States Patent
Fallin et al.

(10) Patent No.: US 7,566,345 B1
(45) Date of Patent: *Jul. 28, 2009

(54) PROSTHESIS FOR THE REPLACEMENT OF A POSTERIOR ELEMENT OF A VERTEBRA

(75) Inventors: T. Wade Fallin, Hyde Park, UT (US); E. Marlowe Goble, Logan, UT (US); Robert W. Hoy, Essex Junction, VT (US)

(73) Assignee: Facet Solutions, Inc, Hopkinton, MA (US)

( * ) Notice: Subject to any disclaimer, the term of this patent is extended or adjusted under 35 U.S.C. 154(b) by 345 days.

This patent is subject to a terminal disclaimer.

(21) Appl. No.: 11/083,710

(22) Filed: Mar. 18, 2005

Related U.S. Application Data

(63) Continuation of application No. 10/196,716, filed on Jul. 16, 2002, now Pat. No. 6,902,580, which is a continuation of application No. 09/797,309, filed on Mar. 1, 2001, now Pat. No. 6,419,703.

(51) Int. Cl.
*A61F 2/44* (2006.01)
*A61B 17/70* (2006.01)
(52) U.S. Cl. .................. 623/17.11; 623/17.16; 606/248
(58) Field of Classification Search ............. 623/17.11, 623/17.16, 17.15, 17.13, 16.11, 18.11; 606/60, 606/61, 70, 71, 248
See application file for complete search history.

(56) References Cited

U.S. PATENT DOCUMENTS

| | | |
|---|---|---|
| 3,426,364 A | 2/1969 | Lumb |
| 3,486,505 A | 12/1969 | Morrison |
| 3,508,954 A | 4/1970 | White et al. |
| 3,648,691 A | 3/1972 | Lumb et al. |
| 3,857,642 A | 12/1974 | Miller |
| 3,867,728 A | 2/1975 | Stubstad et al. |
| 3,875,595 A | 4/1975 | Froning |
| 4,003,376 A | 1/1977 | McKay |
| 4,092,078 A | 5/1978 | Klotz et al. |
| 4,289,123 A | 9/1981 | Dunn |
| 4,349,921 A | 9/1982 | Kuntz |
| 4,369,769 A | 1/1983 | Edwards |
| 4,479,491 A | 10/1984 | Martin |
| 4,483,334 A | 11/1984 | Murray |

(Continued)

FOREIGN PATENT DOCUMENTS

CN  2386790 Y  7/2000

(Continued)

OTHER PUBLICATIONS

Todd Anres; *Facet Joint Arthroplasty: A Glimpse of the Future of Spine Technology*, Othopaedic Product News, Sep./Oct. 2005 p. 38,40.

(Continued)

*Primary Examiner*—Pedro Philogene
(74) *Attorney, Agent, or Firm*—David W. Meibos; Barbara Daniels; Daniel F. Justin

(57) ABSTRACT

A prosthetic replacement for a posterior element of a vertebra comprising portions that replace the natural lamina and the four natural facets. The prosthetic replacement may also include portions that replace one or more of the natural spinous process and the two natural transverse processes. If desired, the prosthesis replacement may also replace the natural pedicles. A method for replacing a posterior element of a vertebra is also provided.

18 Claims, 19 Drawing Sheets

U.S. PATENT DOCUMENTS

| | | |
|---|---|---|
| 4,501,269 A | 2/1985 | Bagby |
| 4,554,914 A | 11/1985 | Kapp et al. |
| 4,599,086 A | 7/1986 | Doty |
| 4,604,995 A | 8/1986 | Stephens et al. |
| 4,611,581 A | 9/1986 | Steffee |
| 4,641,636 A | 2/1987 | Cotrel |
| 4,653,481 A | 3/1987 | Howland et al. |
| 4,657,550 A | 4/1987 | Daher |
| 4,696,290 A | 9/1987 | Steffee |
| 4,743,260 A | 5/1988 | Burton |
| 4,759,769 A | 7/1988 | Hedman et al. |
| 4,772,287 A | 9/1988 | Ray et al. |
| 4,790,303 A | 12/1988 | Steffee |
| 4,800,874 A | 1/1989 | David et al. |
| 4,805,602 A | 2/1989 | Puno et al. |
| 4,827,918 A | 5/1989 | Olerud |
| 4,863,476 A | 9/1989 | Shepperd |
| 4,863,477 A | 9/1989 | Monson |
| 4,892,545 A | 1/1990 | Day et al. |
| 4,904,260 A | 2/1990 | Ray et al. |
| 4,911,718 A | 3/1990 | Lee et al. |
| 4,946,458 A | 8/1990 | Harms et al. |
| 4,955,908 A | 9/1990 | Frey et al. |
| 5,011,484 A | 4/1991 | Breard |
| 5,015,255 A | 5/1991 | Kuslich |
| 5,047,055 A | 9/1991 | Bao et al. |
| 5,071,437 A | 12/1991 | Steffee |
| 5,092,866 A | 3/1992 | Breard et al. |
| 5,092,867 A | 3/1992 | Harms et al. |
| 5,092,893 A | 3/1992 | Smith |
| 5,127,912 A | 7/1992 | Ray et al. |
| 5,129,900 A | 7/1992 | Asher et al. |
| 5,147,361 A | 9/1992 | Ojima et al. |
| 5,147,404 A | 9/1992 | Downey |
| 5,171,279 A | 12/1992 | Mathews |
| 5,171,280 A | 12/1992 | Baumgartner |
| 5,180,393 A | 1/1993 | Commarmond |
| 5,192,326 A | 3/1993 | Bao et al. |
| 5,236,460 A | 8/1993 | Barber |
| 5,246,458 A | 9/1993 | Graham |
| 5,258,031 A | 11/1993 | Salib et al. |
| 5,261,910 A | 11/1993 | Warden et al. |
| 5,263,953 A | 11/1993 | Bagby |
| 5,282,863 A | 2/1994 | Burton |
| 5,304,178 A | 4/1994 | Stahurski |
| 5,306,275 A | 4/1994 | Bryan |
| 5,306,308 A | 4/1994 | Gross et al. |
| 5,306,309 A | 4/1994 | Wagner et al. |
| 5,313,962 A | 5/1994 | Obenchain |
| 5,318,567 A | 6/1994 | Vichard |
| 5,360,430 A | 11/1994 | Lin |
| 5,366,455 A | 11/1994 | Dove et al. |
| 5,370,697 A | 12/1994 | Baumgartner |
| 5,375,823 A | 12/1994 | Navas |
| 5,387,213 A | 2/1995 | Breard et al. |
| 5,391,168 A | 2/1995 | Sanders et al. |
| 5,401,269 A | 3/1995 | Buttner-Janz et al. |
| 5,415,661 A | 5/1995 | Holmes |
| 5,437,669 A | 8/1995 | Yuan et al. |
| 5,437,672 A | 8/1995 | Alleyne |
| 5,439,464 A | 8/1995 | Shapiro |
| 5,443,516 A | 8/1995 | Albrektsson et al. |
| 5,456,722 A | 10/1995 | Mcleod et al. |
| 5,458,641 A | 10/1995 | Ramirez Jimenez |
| 5,458,642 A | 10/1995 | Beer et al. |
| 5,458,643 A | 10/1995 | Oka et al. |
| 5,464,439 A | 11/1995 | Gendler |
| 5,470,333 A | 11/1995 | Ray |
| 5,476,463 A | 12/1995 | Boachie-Adjei et al. |
| 5,480,401 A | 1/1996 | Navas |
| 5,489,308 A | 2/1996 | Kuslich et al. |
| 5,496,318 A | 3/1996 | Howland et al. |
| 5,507,745 A | 4/1996 | Logroscino et al. |
| 5,507,813 A | 4/1996 | Dowd et al. |
| 5,514,180 A | 5/1996 | Heggeness et al. |
| 5,522,899 A | 6/1996 | Michelson |
| 5,527,312 A * | 6/1996 | Ray .............................. 606/61 |
| 5,531,745 A | 7/1996 | Ray |
| 5,531,747 A | 7/1996 | Ray |
| 5,534,028 A | 7/1996 | Bao et al. |
| 5,534,030 A | 7/1996 | Navarro et al. |
| 5,534,031 A | 7/1996 | Matsuzaki et al. |
| 5,540,688 A | 7/1996 | Navas |
| 5,545,166 A | 8/1996 | Howland |
| 5,545,229 A | 8/1996 | Parsons et al. |
| 5,549,607 A | 8/1996 | Olson et al. |
| 5,556,431 A | 9/1996 | Buttner-Janz |
| 5,556,687 A | 9/1996 | McMillin |
| 5,562,735 A | 10/1996 | Margulies |
| 5,562,736 A | 10/1996 | Ray et al. |
| 5,562,737 A | 10/1996 | Graf |
| 5,569,248 A | 10/1996 | Mathews |
| 5,571,189 A | 11/1996 | Kuslich |
| 5,571,191 A | 11/1996 | Fitz |
| 5,572,191 A | 11/1996 | Lundberg |
| 5,582,612 A | 12/1996 | Lin |
| 5,584,832 A | 12/1996 | Schlapfer |
| 5,603,713 A | 2/1997 | Aust et al. |
| 5,609,634 A | 3/1997 | Voydeville |
| 5,645,597 A | 7/1997 | Krapiva |
| 5,645,599 A | 7/1997 | Samani |
| 5,649,926 A | 7/1997 | Howland |
| 5,653,762 A | 8/1997 | Pisharodi |
| 5,666,243 A | 9/1997 | Brent |
| 5,672,175 A | 9/1997 | Martin |
| 5,674,295 A | 10/1997 | Ray et al. |
| 5,674,296 A | 10/1997 | Bryan |
| 5,676,701 A | 10/1997 | Yuan et al. |
| 5,681,310 A | 10/1997 | Yuan et al. |
| 5,683,464 A | 11/1997 | Wagner et al. |
| 5,683,465 A | 11/1997 | Shinn et al. |
| 5,688,272 A | 11/1997 | Montague et al. |
| 5,690,629 A | 11/1997 | Asher et al. |
| 5,702,392 A | 12/1997 | Wu et al. |
| 5,702,450 A | 12/1997 | Bisserie |
| 5,702,453 A | 12/1997 | Rabbe et al. |
| 5,704,936 A | 1/1998 | Mazel |
| 5,713,900 A | 2/1998 | Benzel et al. |
| 5,716,415 A | 2/1998 | Steffee |
| 5,725,582 A | 3/1998 | Bevan et al. |
| 5,728,097 A | 3/1998 | Mathews |
| 5,735,899 A | 4/1998 | Schwartz et al. |
| 5,749,873 A | 5/1998 | Fairley |
| 5,755,796 A | 5/1998 | Ibo et al. |
| 5,772,661 A | 6/1998 | Michelson |
| 5,797,909 A | 8/1998 | Michelson |
| 5,814,046 A | 9/1998 | Hopf |
| 5,824,093 A | 10/1998 | Ray et al. |
| 5,824,094 A | 10/1998 | Serhan et al. |
| 5,836,948 A | 11/1998 | Zucherman et al. |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,888,223 A | 3/1999 | Bray, Jr. |
| 5,893,889 A | 4/1999 | Harrington |
| RE36,221 E | 6/1999 | Breard et al. |
| 5,916,267 A | 6/1999 | Tienboon |
| 5,951,555 A | 9/1999 | Rehak et al. |
| 5,961,516 A | 10/1999 | Graf |
| 5,986,169 A | 11/1999 | Gjunter |
| 6,001,130 A | 12/1999 | Bryan et al. |
| 6,004,322 A | 12/1999 | Bernstein |
| 6,014,588 A | 1/2000 | Fitz |

| | | | | | | |
|---|---|---|---|---|---|---|
| 6,019,759 A | 2/2000 | Rogozinski | | 6,626,909 B2 | 9/2003 | Chin |
| 6,019,792 A | 2/2000 | Cauthen | | 6,626,944 B1 | 9/2003 | Taylor |
| 6,039,761 A | 3/2000 | Li et al. | | 6,652,527 B2 | 11/2003 | Zucherman et al. |
| 6,039,763 A | 3/2000 | Shelokov | | 6,652,534 B2 | 11/2003 | Zucherman et al. |
| 6,048,342 A | 4/2000 | Zucherman et al. | | 6,652,585 B2 | 11/2003 | Lange |
| 6,063,088 A | 5/2000 | Winslow | | 6,669,729 B2 | 12/2003 | Chin |
| 6,063,121 A | 5/2000 | Xavier et al. | | 6,695,842 B2 | 2/2004 | Zucherman et al. |
| 6,066,325 A | 5/2000 | Wallace et al. | | 6,699,246 B2 | 3/2004 | Zucherman et al. |
| 6,068,630 A | 5/2000 | Zucherman et al. | | 6,699,247 B2 | 3/2004 | Zucherman et al. |
| RE36,758 E * | 6/2000 | Fitz .................. 623/17.11 | | 6,733,534 B2 | 5/2004 | Sherman |
| 6,074,390 A | 6/2000 | Zucherman et al. | | 6,761,719 B2 | 7/2004 | Justis et al. |
| 6,080,157 A | 6/2000 | Cathro et al. | | 6,761,720 B1 | 7/2004 | Senegas |
| 6,090,112 A | 7/2000 | Zucherman et al. | | 6,783,527 B2 | 8/2004 | Drewry et al. |
| 6,093,205 A | 7/2000 | McLeod et al. | | 6,796,983 B1 | 9/2004 | Zucherman et al. |
| 6,113,637 A | 9/2000 | Gill et al. | | 6,811,567 B2 | 11/2004 | Reiley |
| 6,113,639 A | 9/2000 | Ray et al. | | 6,835,205 B2 | 12/2004 | Atkinson et al. |
| 6,132,464 A * | 10/2000 | Martin ............... 623/17.15 | | 6,835,207 B2 | 12/2004 | Zacouto et al. |
| 6,132,465 A | 10/2000 | Ray et al. | | 7,087,084 B2 * | 8/2006 | Reiley .................. 623/17.11 |
| 6,146,421 A | 11/2000 | Gordon et al. | | 7,090,698 B2 * | 8/2006 | Goble et al. ........... 623/17.11 |
| 6,149,652 A | 11/2000 | Zucherman et al. | | 2001/0007073 A1 | 7/2001 | Zucherman et al. |
| 6,151,934 A | 11/2000 | Chong et al. | | 2001/0012938 A1 | 8/2001 | Zucherman et al. |
| 6,152,926 A | 11/2000 | Zucherman et al. | | 2001/0016743 A1 | 8/2001 | Zucherman et al. |
| 6,156,038 A | 12/2000 | Zucherman et al. | | 2001/0021850 A1 | 9/2001 | Zucherman et al. |
| 6,156,067 A | 12/2000 | Bryan et al. | | 2001/0031965 A1 | 10/2001 | Zucherman et al. |
| 6,176,861 B1 | 1/2001 | Bernstein et al. | | 2001/0039452 A1 | 11/2001 | Zucherman et al. |
| 6,179,838 B1 | 1/2001 | Fiz | | 2002/0029039 A1 | 3/2002 | Zucherman et al. |
| 6,183,471 B1 | 2/2001 | Zucherman et al. | | 2002/0065557 A1 | 5/2002 | Goble et al. |
| 6,190,387 B1 | 2/2001 | Zucherman et al. | | 2002/0072800 A1 | 6/2002 | Goble et al. |
| 6,190,414 B1 | 2/2001 | Young et al. | | 2002/0091446 A1 | 7/2002 | Zucherman et al. |
| 6,206,882 B1 | 3/2001 | Cohen | | 2002/0099384 A1 | 7/2002 | Scribner et al. |
| 6,206,922 B1 | 3/2001 | Zdeblick et al. | | 2002/0116000 A1 | 8/2002 | Zucherman et al. |
| 6,228,118 B1 | 5/2001 | Gordon | | 2002/0123806 A1 | 9/2002 | Reiley |
| 6,235,030 B1 | 5/2001 | Zucherman et al. | | 2002/0143331 A1 | 10/2002 | Zucherman et al. |
| 6,238,397 B1 | 5/2001 | Zucherman et al. | | 2002/0151895 A1 | 10/2002 | Soboleski et al. |
| 6,241,730 B1 | 6/2001 | Alby | | 2002/0183746 A1 | 12/2002 | Zucherman et al. |
| 6,264,655 B1 | 7/2001 | Pisharodi | | 2003/0004572 A1 | 1/2003 | Goble et al. |
| 6,267,764 B1 | 7/2001 | Elberg | | 2003/0009226 A1 | 1/2003 | Graf |
| 6,280,444 B1 | 8/2001 | Zucherman et al. | | 2003/0028250 A1 | 2/2003 | Reiley et al. |
| 6,290,700 B1 | 9/2001 | Schmotzer | | 2003/0040797 A1 | 2/2003 | Fallin et al. |
| 6,293,949 B1 | 9/2001 | Justis et al. | | 2003/0055427 A1 | 3/2003 | Graf |
| 6,312,469 B1 | 11/2001 | Gielen et al. | | 2003/0065330 A1 | 4/2003 | Zucherman et al. |
| 6,314,325 B1 | 11/2001 | Fitz | | 2003/0073998 A1 | 4/2003 | Pagliuca et al. |
| 6,332,882 B1 | 12/2001 | Zucherman et al. | | 2003/0109880 A1 | 6/2003 | Shirado et al. |
| 6,332,883 B1 | 12/2001 | Zucherman et al. | | 2003/0153912 A1 | 8/2003 | Graf |
| 6,379,355 B1 | 4/2002 | Zucherman et al. | | 2003/0191470 A1 | 10/2003 | Ritland |
| 6,402,750 B1 | 6/2002 | Atkinson et al. | | 2003/0220642 A1 | 11/2003 | Freudiger |
| 6,413,259 B1 | 7/2002 | Lyons et al. | | 2003/0220643 A1 | 11/2003 | Ferree |
| 6,419,676 B1 | 7/2002 | Zucherman et al. | | 2004/0006341 A1 | 1/2004 | Shaolian et al. |
| 6,419,677 B2 | 7/2002 | Zucherman et al. | | 2004/0006391 A1 | 1/2004 | Reiley |
| 6,419,703 B1 * | 7/2002 | Fallin et al. ............. 623/17.11 | | 2004/0009232 A1 | 1/2004 | Reiner |
| 6,419,704 B1 | 7/2002 | Ferree | | 2004/0024458 A1 | 2/2004 | Senegas et al. |
| 6,440,169 B1 | 8/2002 | Elberg et al. | | 2004/0049189 A1 | 3/2004 | Le Couedic et al. |
| 6,447,546 B1 | 9/2002 | Bramlet et al. | | 2004/0049190 A1 | 3/2004 | Biedermann et al. |
| 6,451,019 B1 | 9/2002 | Zucherman et al. | | 2004/0049272 A1 | 3/2004 | Reiley |
| 6,451,020 B1 | 9/2002 | Zucherman et al. | | 2004/0049273 A1 | 3/2004 | Reiley |
| 6,458,131 B1 | 10/2002 | Ray | | 2004/0049274 A1 | 3/2004 | Reiley |
| 6,461,359 B1 | 10/2002 | Tribus et al. | | 2004/0049275 A1 | 3/2004 | Reiley |
| 6,471,704 B2 | 10/2002 | Gertzbein et al. | | 2004/0049276 A1 | 3/2004 | Reiley |
| 6,475,219 B1 | 11/2002 | Shelokov | | 2004/0049277 A1 | 3/2004 | Reiley |
| 6,478,796 B2 | 11/2002 | Zucherman et al. | | 2004/0049278 A1 | 3/2004 | Reiley |
| 6,481,440 B2 | 11/2002 | Gielen et al. | | 2004/0049281 A1 | 3/2004 | Reiley |
| 6,485,518 B1 | 11/2002 | Cornwall et al. | | 2004/0073215 A1 | 4/2004 | Carli |
| 6,500,178 B2 | 12/2002 | Zucherman et al. | | 2004/0078082 A1 | 4/2004 | Lange |
| 6,514,256 B2 | 2/2003 | Zucherman et al. | | 2004/0082954 A1 | 4/2004 | Teitelbaum et al. |
| 6,527,806 B2 | 3/2003 | Ralph et al. | | 2004/0087950 A1 | 5/2004 | Teitelbaum |
| 6,540,747 B1 | 4/2003 | Marino | | 2004/0106995 A1 | 6/2004 | Le Couedic et al. |
| 6,540,785 B1 | 4/2003 | Gill et al. | | 2004/0111154 A1 | 6/2004 | Reiley |
| 6,565,605 B2 | 5/2003 | Goble et al. | | 2004/0116927 A1 | 6/2004 | Graf |
| 6,579,319 B2 | 6/2003 | Goble et al. | | 2004/0117017 A1 | 6/2004 | Pasquet et al. |
| 6,582,433 B2 | 6/2003 | Yun | | 2004/0127989 A1 | 7/2004 | Dooris et al. |
| 6,585,769 B1 | 7/2003 | Muhanna et al. | | 2004/0143264 A1 | 7/2004 | Mcafee |
| 6,610,091 B1 * | 8/2003 | Reiley .................. 623/17.11 | | 2004/0147928 A1 | 7/2004 | Landry et al. |
| 6,616,669 B2 | 9/2003 | Ogilvie et al. | | 2004/0153071 A1 | 8/2004 | Zucherman et al. |

| | | |
|---|---|---|
| 2004/0158245 A1 | 8/2004 | Chin |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0186475 A1 | 9/2004 | Falahee |
| 2004/0220568 A1 | 11/2004 | Zucherman et al. |
| 2004/0225289 A1 | 11/2004 | Biedermann et al. |
| 2004/0230192 A1 | 11/2004 | Graf |
| 2004/0230201 A1 | 11/2004 | Yuan et al. |
| 2004/0230304 A1 | 11/2004 | Yuan et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2005/0010291 A1 | 1/2005 | Stinson et al. |
| 2005/0010293 A1 | 1/2005 | Zucherman et al. |
| 2005/0010298 A1 | 1/2005 | Zucherman et al. |
| 2005/0027361 A1 | 2/2005 | Reiley |
| 2005/0033434 A1 | 2/2005 | Berry |
| 2005/0033439 A1 | 2/2005 | Gordon et al. |
| 2005/0043797 A1 | 2/2005 | Lee |
| 2005/0043799 A1 | 2/2005 | Reiley |
| 2005/0113927 A1 | 5/2005 | Malek |
| 2005/0119748 A1 | 6/2005 | Reiley et al. |
| 2005/0131406 A1 | 6/2005 | Reiley et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0154467 A1 | 7/2005 | Peterman et al. |
| 2005/0171609 A1 | 8/2005 | Humphreys |

FOREIGN PATENT DOCUMENTS

| | | |
|---|---|---|
| EP | 408489 A1 | 1/1991 |
| EP | 322334 B1 | 2/1992 |
| EP | 667127 A1 | 8/1995 |
| EP | 767637 B1 | 11/1998 |
| EP | 768843 B1 | 2/1999 |
| EP | 669109 B1 | 5/1999 |
| EP | 1299042 A2 | 4/2003 |
| EP | 1303224 A1 | 4/2003 |
| EP | 1303225 A1 | 4/2003 |
| EP | 1414358 A2 | 5/2004 |
| EP | 1448109 A2 | 8/2004 |
| EP | 1239785 B1 | 9/2004 |
| EP | 1343424 B1 | 9/2004 |
| EP | 1399078 B1 | 12/2004 |
| JP | 10179622 A2 | 7/1998 |
| JP | 10277070 A2 | 10/1998 |
| SU | 1468543 A1 | 3/1989 |
| SU | 1517953 A1 | 10/1989 |
| WO | WO2008707827 A1 | 12/1987 |
| WO | WO9421185 A1 | 9/1994 |
| WO | WO9505783 A1 | 3/1995 |
| WO | WO9505784 A1 | 3/1995 |
| WO | WO9505785 A1 | 3/1995 |
| WO | WO9505786 A1 | 3/1995 |
| WO | WO9600049 A1 | 1/1996 |
| WO | WO9822033 A1 | 5/1998 |
| WO | WO9848707 A1 | 11/1998 |
| WO | WO9848717 A1 | 11/1998 |
| WO | WO9856301 A1 | 12/1998 |
| WO | WO9905995 A1 | 2/1999 |
| WO | WO9921500 A1 | 5/1999 |
| WO | WO9921501 A1 | 5/1999 |
| WO | WO9923963 A1 | 5/1999 |
| WO | WO9960957 C2 | 12/1999 |
| WO | WO9965412 A1 | 12/1999 |
| WO | WO0038582 | 7/2000 |
| WO | WO0062684 A1 | 10/2000 |
| WO | WO0130248 A1 | 5/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0197721 A3 | 12/2001 |
| WO | WO0200124 A1 | 1/2002 |
| WO | WO0203882 A2 | 1/2002 |
| WO | WO0207621 A1 | 1/2002 |
| WO | WO0207622 A1 | 1/2002 |
| WO | WO0207623 A1 | 1/2002 |
| WO | WO0213732 A3 | 2/2002 |
| WO | WO0230336 A2 | 4/2002 |
| WO | WO0234120 A2 | 5/2002 |
| WO | WO0243603 A1 | 6/2002 |
| WO | WO02067792 A2 | 9/2002 |
| WO | WO02067793 A2 | 9/2002 |
| WO | WO02089712 A1 | 11/2002 |
| WO | WO02089712 A2 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004032794 A3 | 4/2004 |
| WO | WO2004039239 A2 | 5/2004 |
| WO | WO2004039239 A3 | 5/2004 |
| WO | WO2004039243 A2 | 5/2004 |
| WO | WO2004039243 A3 | 5/2004 |
| WO | WO2004041066 A2 | 5/2004 |
| WO | WO2004041066 A3 | 5/2004 |
| WO | WO2004073533 A1 | 9/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |
| WO | WO2006102443 | 9/2006 |

OTHER PUBLICATIONS

Goh JC, et al., "Influence of PLIF cage size on lumbar spine stability", Spine, Jan. 2001 25:1, PubMed abstract.

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compresive strength of posterior lumbar interbody fusion implants", Spine, Aug. 1, 2000 25:15, PubMed abstract.

* cited by examiner

PROSTHESIS FOR THE REPLACEMENT OF A POSTERIOR ELEMENT OF A VERTEBRA

CROSS-REFERENCE TO RELATED APPLICATIONS

This application is a continuation of:

U.S. application Ser. No. 10/196,716, filed Jul. 16, 2002 now U.S. Pat. No. 6,902,580, and is entitled PROSTHESIS FOR THE REPLACEMENT OF A POSTERIOR ELEMENT OF A VERTEBRA.

The foregoing is a continuation of:

U.S. application Ser. No. 09/797,309, filed Mar. 1, 2001, and is entitled PROSTHESIS FOR THE REPLACEMENT OF A POSTERIOR ELEMENT OF A VERTEBRA and has issued as U.S. Pat. No. 6,419,703.

All of the foregoing are incorporated herein by reference.

BACKGROUND OF THE INVENTION

1. Field of the Invention

The present invention relates to surgical devices and methods in general, and more particularly to surgical devices and methods for restoring a damaged, diseased or otherwise painful spinal joint.

2. Description Of Related Art

Traumatic, inflammatory, metabolic, synovial, neoplastic and degenerative disorders of the spine can produce debilitating pain that can have severe socioeconomic and psychological effects.

One of the most common surgical interventions today is arthrodesis, or spine fusion, in which two or more adjacent vertebral bodies are fused together in order to alleviate pain associated with the disc(s) located between those vertebral bodies. Approximately 300,000 such procedures are performed annually in the United States alone. Clinical success varies considerably, depending upon technique and indications, and consideration must be given to the concomitant risks and complications.

For example, while spine fusion generally helps to eliminate certain types of pain, it has also been shown to decrease function by limiting the range of motion for patients in flexion, extension, rotation and lateral bending. Furthermore, it is believed that spine fusion creates increased stresses on (and, therefore, accelerated degeneration of) adjacent non-fused motion segments. Additionally, pseudoarthrosis, resulting from an incomplete or ineffective fusion, may reduce or even totally eliminate the desired pain relief for the patient. Also, the fusion device(s) used to effect fusion, whether artificial or biological, may migrate out of the fusion site, thereby creating significant new problems for the patient.

Recently, several attempts have been made to recreate the natural biomechanics of the spine through the use of an artificial disc. Artificial discs are intended to restore articulation between vertebral bodies so as to recreate the full range of motion normally allowed by the elastic properties of the natural disc, which directly connects two opposed vertebral bodies. However, the artificial discs developed to date do not adequately address the mechanics of motion of the spinal column.

In addition to the foregoing, posterior elements called the facet joints help to support axial, torsional and shear loads that act on the spinal column. Furthermore, the facet joints are diarthroidal joints that provide both sliding articulation and load transmission features. However, the facet joints can also be a significant source of spinal disorders and, in many cases, debilitating pain. For example, a patient may suffer from arthritic facet joints, severe facet joint tropism or otherwise deformed facet joints, facet joint injuries, etc. There is currently a lack of good interventions for facet joint disorders. Facetectomy, or the removal of the facet joints, may provide some relief, but it is also believed to produce significant decreases in the stiffness of the spinal column (i.e., hypermobility) in all planes of motion: flexion and extension, lateral bending, and rotation. Furthermore, problems with the facet joints can also complicate treatments associated with other portions of the spine. By way of example, contraindications for artificial discs include arthritic facet joints, absent facet joints, severe facet joint tropism or otherwise deformed facet joints.

U.S. Pat. No. Re. 36,758 (Fitz) discloses an artificial facet joint where the inferior facet, the mating superior facet, or both, are covered with a cap. This cap requires no preparation of the bone or articular surfaces; it covers and, therefore, preserves the bony and articular structure.

The capping of the facet has several potential disadvantages, however. If the facet joint is osteoarthritic, a cap will not remove the source of the pain. Additionally, at least in the case of surface replacements for osteoarthritic femoral heads, the capping of articular bone ends has proven to lead to clinical failure by means of mechanical loosening. This clinical failure is hypothesized to be a sequela of disrupting the periosteum and ligamentum teres femoris, both serving a nutrition delivery role to the femoral head, thereby leading to avascular necrosis of the bony support structure for the surface replacement. It is possible that corresponding problems could develop from capping the facet. Another potential disadvantage of facet capping is that in order to accommodate the wide variability in anatomical morphology of the facets, not only between individuals but also between levels within the spinal column, a very wide range of cap sizes and shapes is required.

U.S. Pat. No. 6,132,464 (Martin) discloses a spinal facet joint prosthesis that is supported on the lamina (which is sometimes also referred to as the posterior arch). Extending from this support structure are inferior and/or superior blades that replace the cartilage at the facet joint. Like the design of the aforementioned U.S. Pat. No. Re. 36,758, the prosthesis of U.S. Pat. No. 6,132,464 generally preserves existing bony structures and therefore does not address pathologies which affect the bone of the facets in addition to affecting the associated cartilage. Furthermore, the prosthesis of U.S. Pat. No. 6,132,464 requires a secure mating between the prosthesis and the lamina. However, the lamina is a very complex and highly variable anatomical surface. As a result, in practice, it is very difficult to design a prosthesis that provides reproducible positioning against the lamina so as to correctly locate the cartilage-replacing blades for the facet joints.

Another approach to surgical intervention for spinal facets is disclosed in International Pat. Publication No. WO9848717A1 (Villaret et al.). While this publication teaches the replacement of spinal facets, the replacement is interlocked in a manner so as to immobilize the joint.

Thus it will be seen that previous attempts to provide facet joint replacement have proven inadequate.

In some circumstances, additional structures of a vertebra beside the facets may have been compromised by disease or trauma. For example, the lamina, the spinous process and/or the two transverse processes may have been compromised by disease or trauma. In such a circumstance, it would be useful to have a prosthesis which would allow the replacement of the same.

SUMMARY OF THE INVENTION

As a result, one object of the present invention is to provide a novel prosthesis for the replacement of all four of the facets so as to remove the source of traumatic, arthritic or other disease-mediated pain.

Another object of the present invention is to provide a novel prosthesis for the replacement of different combinations of the posterior elements of a vertebra.

And another object of the present invention is to provide a novel prosthesis for the replacement of a posterior element of a vertebra that replicates the lamina, the four facets, the spinous process and the two transverse processes.

Still another object of the present invention is to provide a novel prosthesis for the replacement of a posterior element of a vertebra that replicates the lamina, the four facets and the spinous process.

Yet another object of the present invention is to provide a novel prosthesis for the replacement of a posterior element of a vertebra that replicates the lamina, the four facets and the two transverse processes.

Another object of the present invention is to provide a novel prosthesis for the replacement of a posterior element of a vertebra that replicates the lamina and the four facets.

And another object of the present invention is to provide a novel prosthesis for the replacement of a posterior element of a vertebra that replicates the two pedicles, the lamina, the four facets, the spinous process and the two transverse processes.

Still another object of the present invention is to provide a novel prosthesis for the replacement of a posterior element of a vertebra that replicates the two pedicles, the lamina, the four facets and the spinous process.

Yet another object of the present invention is to provide a novel prosthesis for the replacement of a posterior element of a vertebra that replicates the two pedicles, the lamina, the four facets and the two transverse processes.

Another object of the present invention is to provide a novel prosthesis for the replacement of a posterior element of a vertebra that replicates the two pedicles, the lamina and the four facets.

These and other objects are addressed by the present invention which, in one preferred embodiment, comprises a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; a pair of prosthetic inferior facets extending from the prosthetic lamina, a prosthetic spinous process extending from the prosthetic lamina; and a pair of prosthetic transverse processes extending from the two prosthetic mounts.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; a pair of prosthetic inferior facets extending from the prosthetic lamina; and a prosthetic spinous process extending from the prosthetic lamina.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; a pair of prosthetic inferior facets extending from the prosthetic lamina; and a pair of prosthetic transverse processes extending from the two prosthetic mounts.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; and a pair of prosthetic inferior facets extending from the prosthetic lamina.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; a pair of prosthetic inferior facets extending from the prosthetic lamina; a prosthetic spinous process extending from the prosthetic lamina; and a pair of prosthetic transverse processes extending from the two prosthetic pedicles.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; a pair of prosthetic inferior facets extending from the prosthetic lamina; and a prosthetic spinous process extending from the prosthetic lamina.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; a pair of prosthetic inferior facets extending from the prosthetic lamina; and a pair of prosthetic transverse processes extending from the two prosthetic pedicles.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; and a pair of prosthetic inferior facets extending from the prosthetic lamina.

In another form of the invention, there is provided a method for replacing a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina a natural spinous process extending from the natural lamina, and a pair of natural transverse processes extending from the two natural pedicles, the method comprising the steps of making a resection at the most dorsal aspect of the two natural pedicles; and attaching a prosthesis to the resected vertebra, the prosthesis comprising a pair of prosthetic mounts, a prosthetic lamina extending from the two prosthetic mounts, a pair of prosthetic superior facets extending from the two prosthetic mounts and the prosthetic lamina, and a pair of prosthetic inferior facets extending from the prosthetic lamina.

In another form of the invention, there is provided a method for replacing a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the natural pedicles, the method comprising the steps of making a resection at the junction of the natural vertebral body and the two natural pedicles; and attaching a prosthesis to the resected vertebra, the prosthesis comprising a pair of prosthetic pedicles, a prosthetic lamina extending from the prosthetic pedicles, a pair of prosthetic superior facets extending from the two prosthetic pedicles and the prosthetic lamina, and a pair of prosthetic inferior facets extending from the prosthetic lamina.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
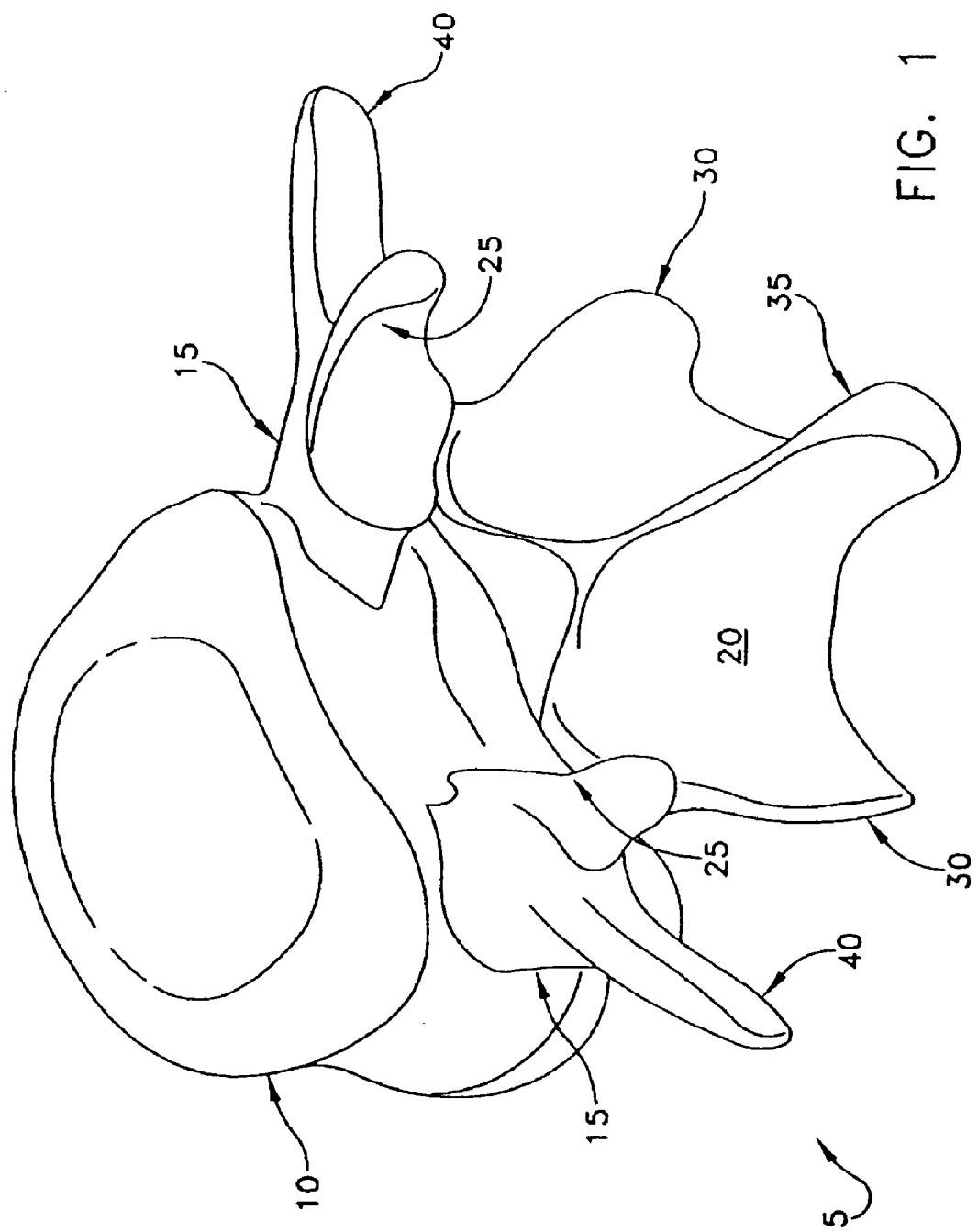
FIG. 1 is a perspective view of a lumbar vertebra.

Referring now to FIG. 1, there is shown a natural lumbar vertebra 5 comprising a natural vertebral body 10, a pair of natural pedicles 15 extending from natural vertebral body 10, a natural lamina 20 extending from natural pedicles 15, a pair of natural superior facets 25 extending from natural pedicles 15 and natural lamina 20, a pair of natural inferior facets 30 extending from natural lamina 20, a natural spinous process 35 extending from natural lamina 20, and a pair of natural transverse processes 40 extending from natural pedicles 15.

Figure 2:
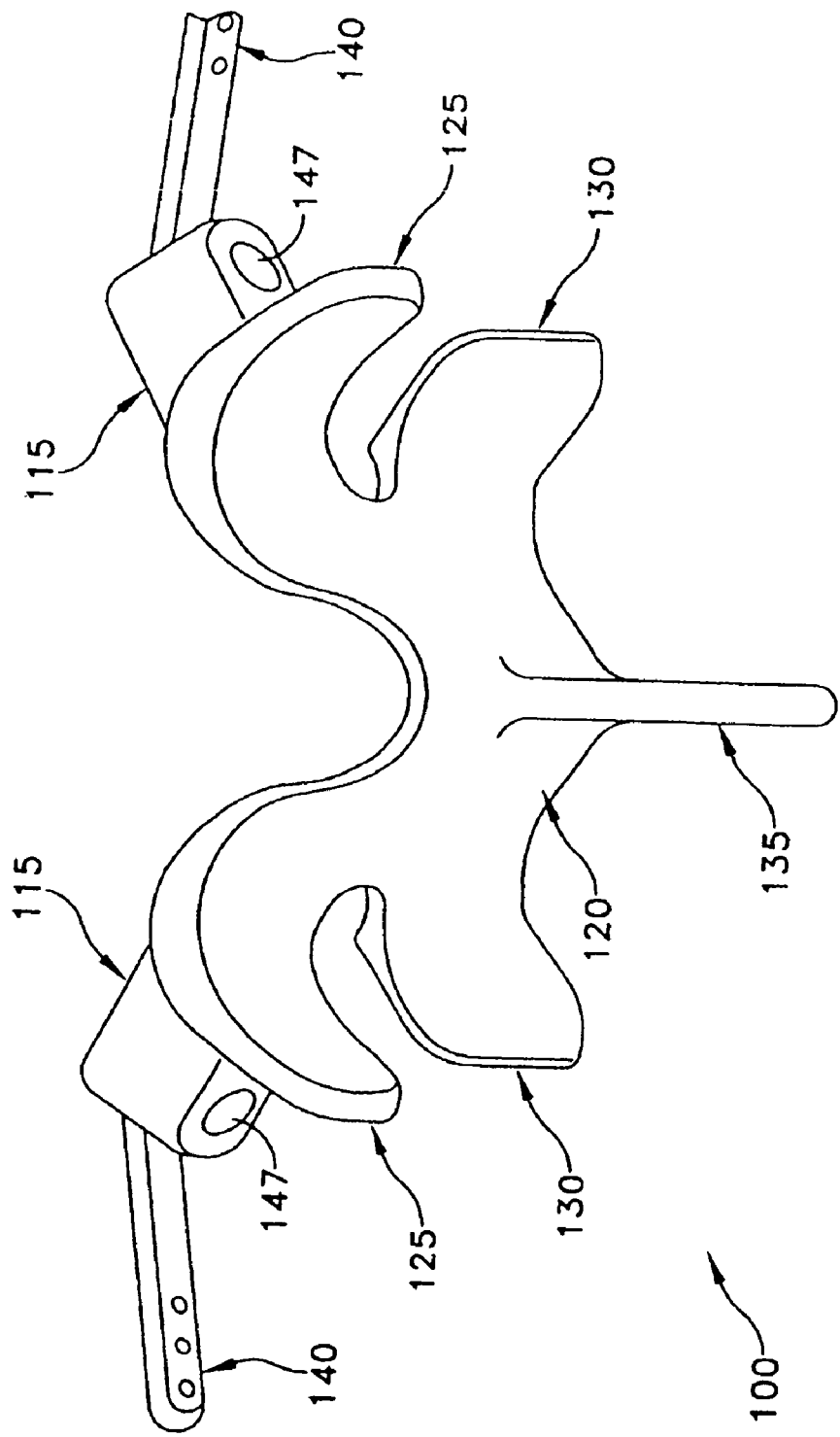
FIG. 2 is a perspective view of a novel prosthesis that replaces the lamina, the four facets, the spinous process and the two transverse processes of a vertebra.
Figure 3:
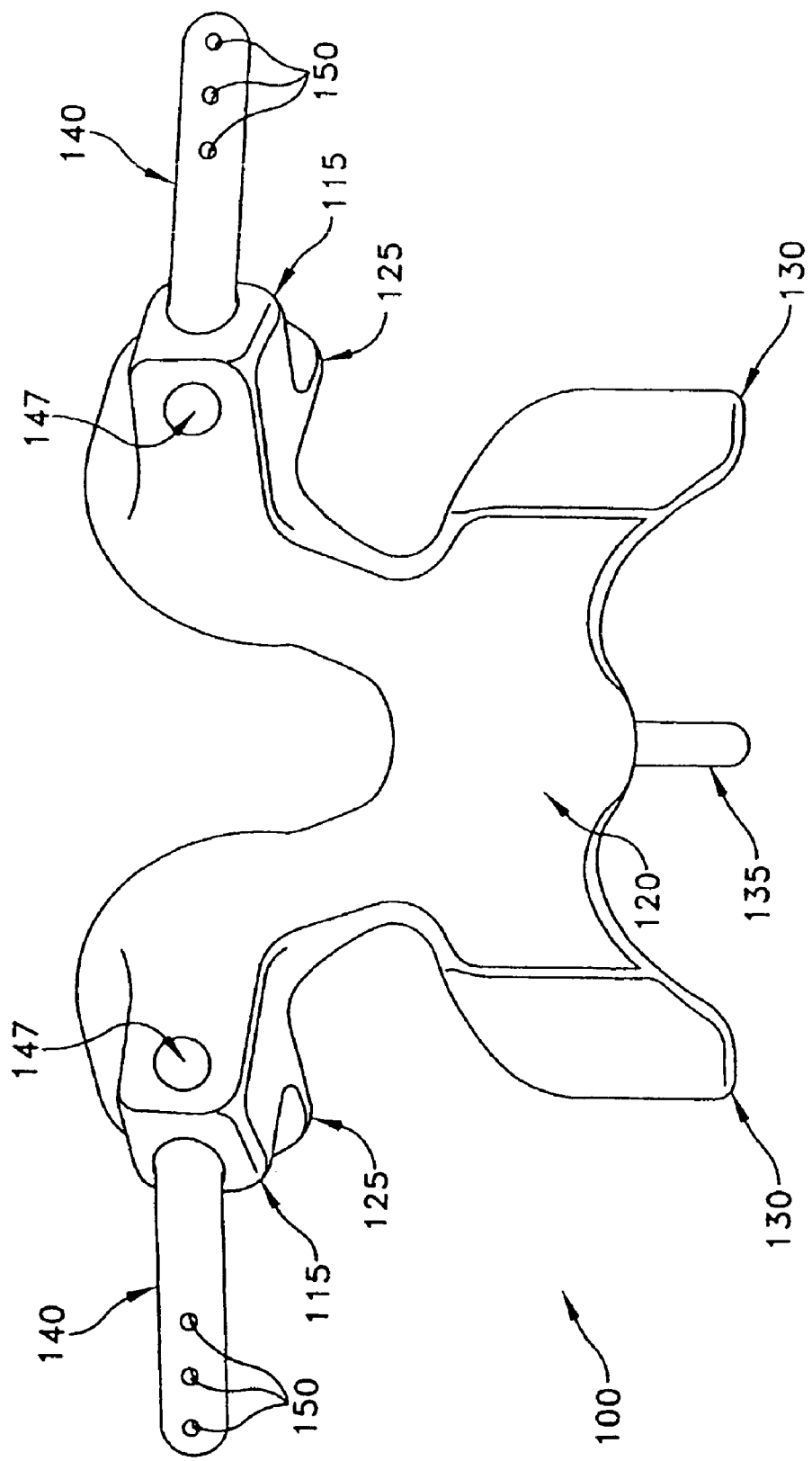
FIG. 3 is an anterior view of the prosthesis shown in FIG. 2.

Looking next at FIGS. 2 and 3, there is shown a novel prosthesis 100 which is adapted to replace the natural lamina 20, the two natural superior facets 25, the two natural inferior facets 30, the natural spinous process 35, and the two natural transverse processes 40. To this end, prosthesis 100 comprises a pair of prosthetic mounts 115, a prosthetic lamina 120 extending from prosthetic mounts 115, a pair of prosthetic superior facets 125 extending from prosthetic mounts 115 and prosthetic lamina 120, a pair of prosthetic inferior facets 130 extending from prosthetic lamina 120, a prosthetic spinous process 135 extending from prosthetic lamina 120, and a pair of prosthetic transverse processes 140 extending from prosthetic mounts 115.

Figure 4:
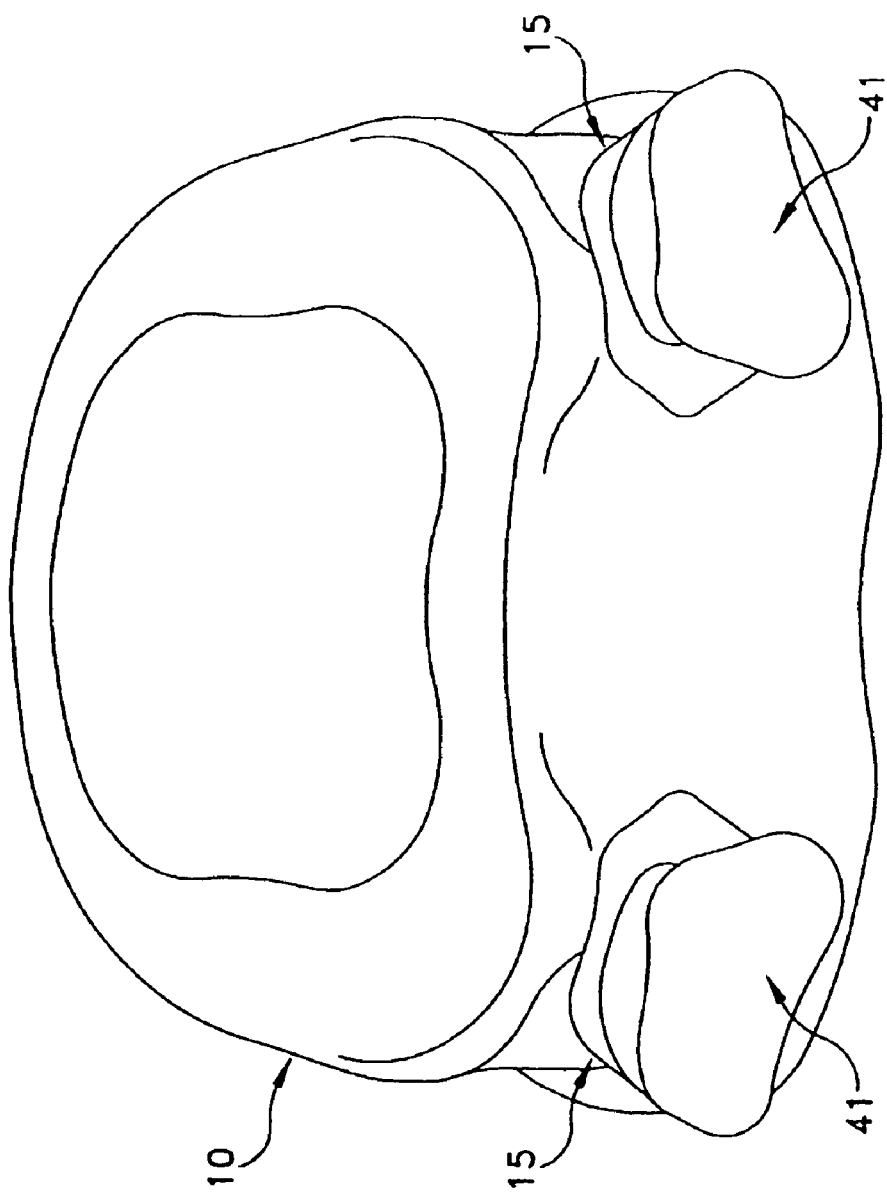
FIG. 4 is a perspective view of a vertebra which has been resected to receive the prosthesis shown in FIG. 2.
Figure 5:
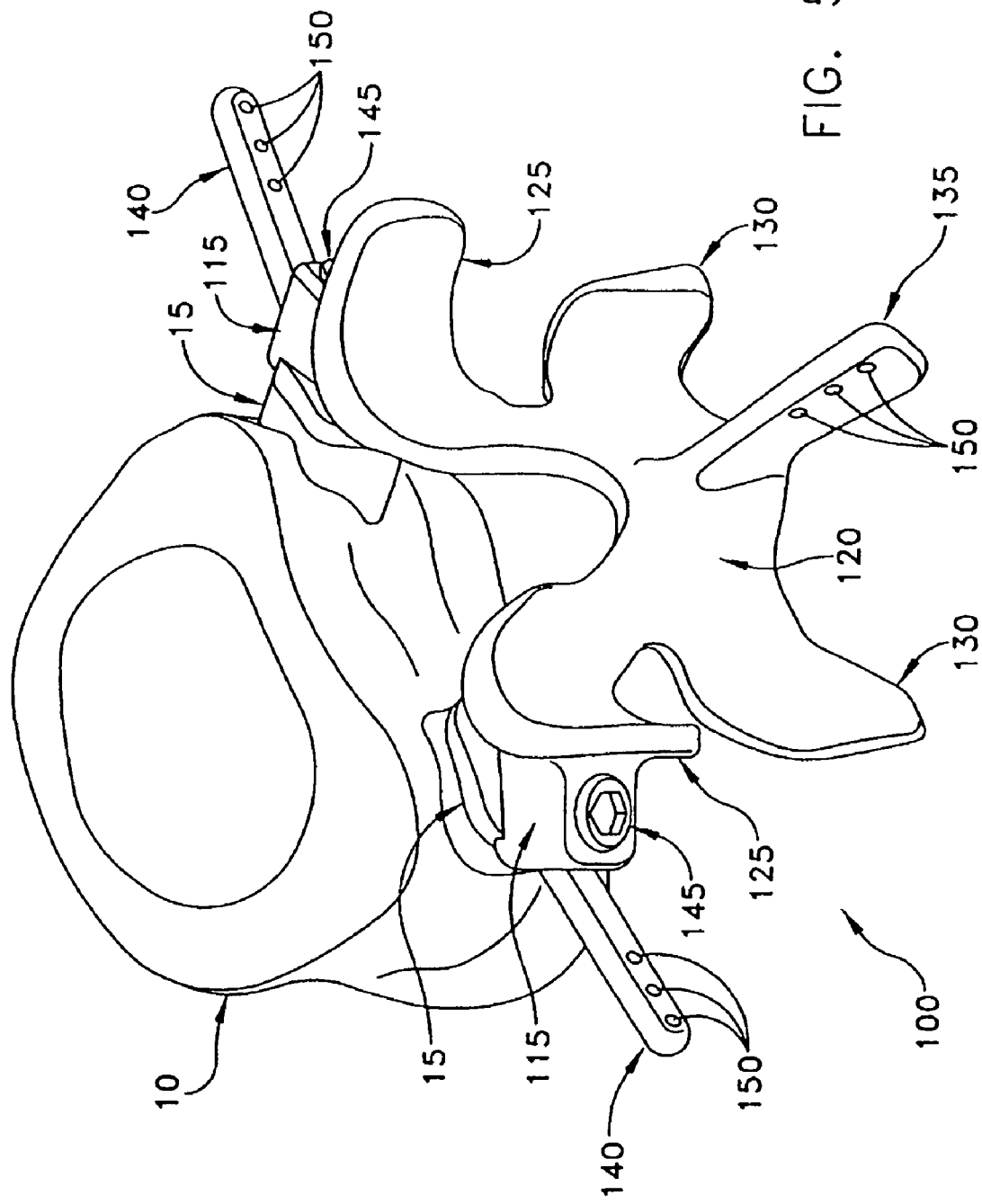
FIG. 5 is a perspective view of the prosthesis shown in FIG. 2 mounted to the resected vertebra shown in FIG. 4.
Figure 6:
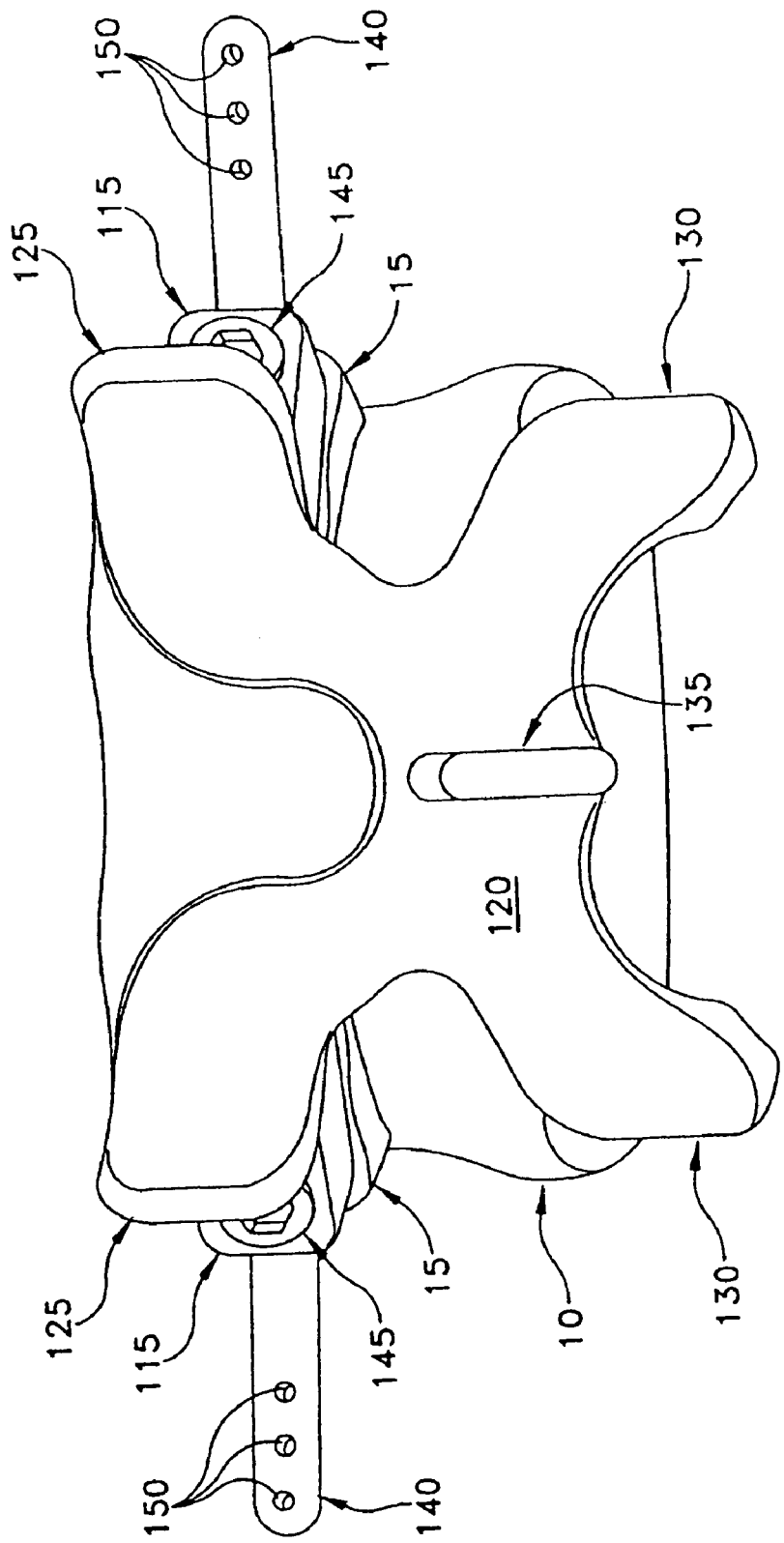
FIG. 6 is a dorsal view of the prosthesis shown in FIG. 2 mounted to the resected vertebra shown in FIG. 4.
Figure 7:
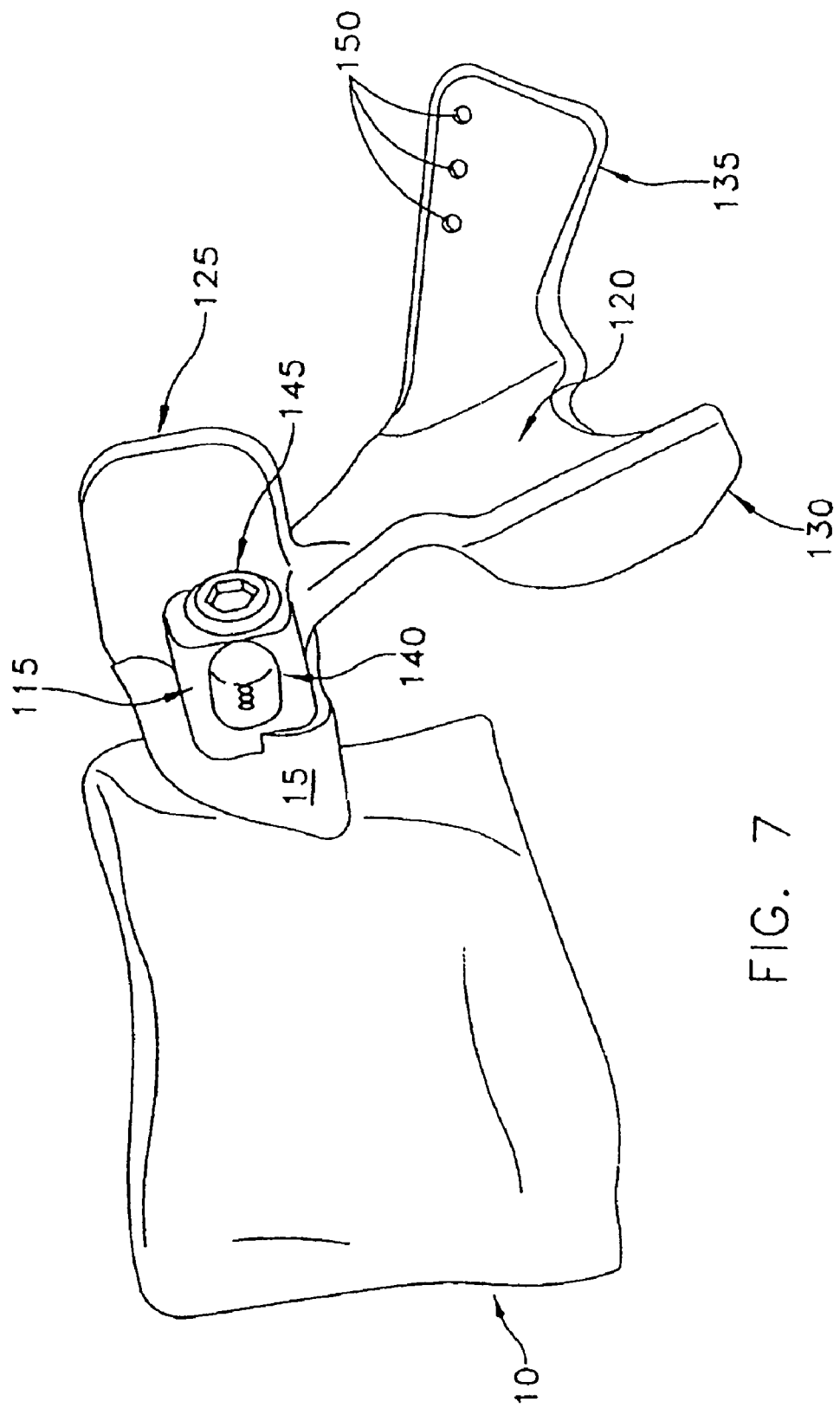
FIG. 7 is a lateral view of the prosthesis shown in FIG. 2 mounted to the resected vertebra shown in FIG. 4.

In the use of prosthesis 100, natural lumbar vertebra 5 is resected at its natural pedicles 15 so as to remove the natural lamina 20, the two natural superior facets 25, the two natural inferior facets 30, the natural spinous process 35, and the two natural transverse processes 40, leaving a pair of pedicle end surfaces 41 (FIG. 4). Then the prosthesis 100 may be attached to the natural pedicles 15, e.g., by placing prosthetic mounts 115 against pedicle surfaces 41 and then passing screws 145 through screw holes 147 and into natural pedicles 15, as shown in FIGS. 5-7. As seen in the drawings, the relative size, shape and positioning of the prosthetic lamina 120, the two prosthetic superior facets 125, the two prosthetic inferior facets 130, the prosthetic spinous process 135, and the two prosthetic transverse processes 140 essentially mimic the relative size, shape and positioning of the natural lamina 20, the two natural superior facets 25, the two natural inferior facets 30, the natural spinous process 35, and the two natural transverse processes 40, whereby to effectively restore the vertebra. If desired, holes 150 may be provided in the prosthetic spinous process 135 and/or the two prosthetic transverse processes 140 so as to facilitate re-attaching soft tissue to these structures.

Figure 8:
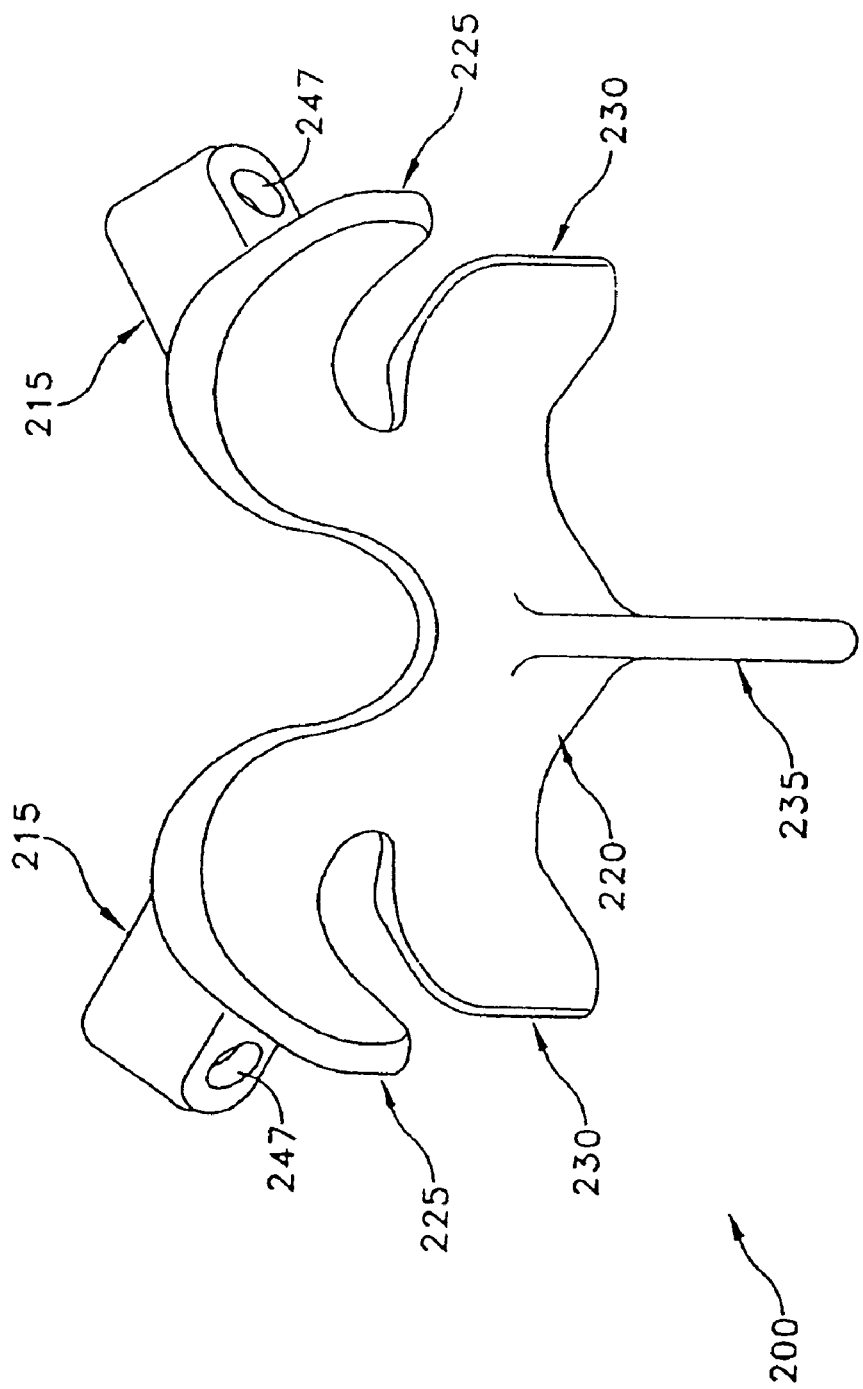
FIG. 8 is a perspective view of a novel prosthesis that replaces the lamina, the four facets and the spinous process of a vertebra.

Looking next at FIG. 8, there is shown a novel prosthesis 200 which is adapted to replace natural lamina 20, the two natural superior facets 25, the two natural inferior facets 30, and natural spinous process 35. To this end, prosthesis 200 comprises a pair of prosthetic mounts 215, a prosthetic lamina 220 extending from prosthetic mounts 215, a pair of prosthetic superior facets 225 extending from prosthetic mounts 215 and prosthetic lamina 220, a pair of prosthetic inferior facets 230 extending from prosthetic lamina 220, and a prosthetic spinous process 235 extending from prosthetic lamina 220.

In the use of prosthesis 200, natural lumbar vertebra 5 is resected at its natural pedicles 15 so as to remove the natural lamina 20, the two natural superior facets 25, the two natural inferior facets 30, the spinous process 35 and the two natural transverse processes 40, leaving a pair of pedicle surfaces 41 (FIG. 4). Then the prosthesis 200 may be attached to the natural pedicles 15, e.g., by placing prosthetic mounts 215 against pedicle surfaces 41 and then passing screws 145 through holes 247 and into natural pedicles 15. As seen in the drawing, the relative size, shape and positioning of prosthetic lamina 220, the two prosthetic superior facets 225, the two prosthetic inferior facets 230, and the prosthetic spinous process 235 essentially mimic the relative size, shape and positioning of the natural lamina 20, the two natural superior facets 25 the two natural inferior facets 30, and the natural spinous process 35, whereby to effectively restore the vertebra. If desired, holes 150 may be provided in the prosthetic spinous process 235 so as to facilitate re-attaching soft tissue to this structure.

Figure 9:
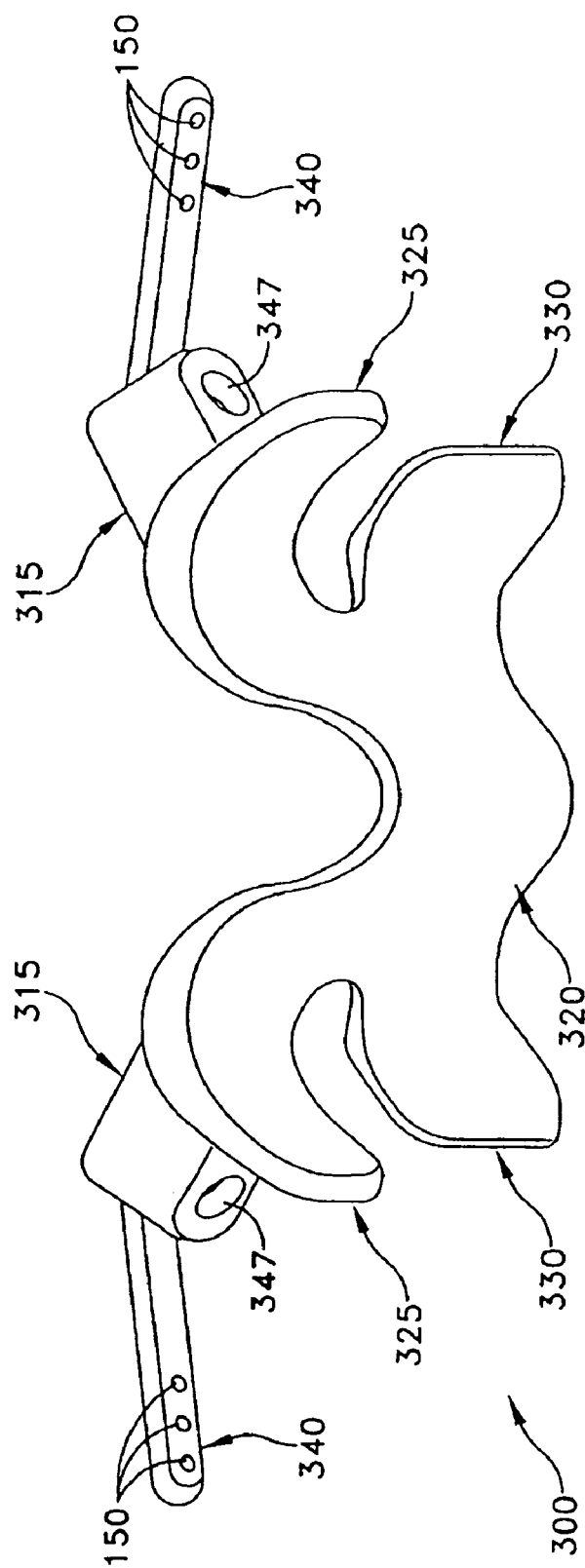
FIG. 9 is a perspective view of a novel prosthesis that replaces the lamina, the four facets and the two transverse processes of a vertebra.

Looking next at FIG. 9, there is shown a novel prosthesis 300 which is adapted to replace the natural lamina 20, the two natural superior facets 25, the two natural inferior facets 30, and the two natural transverse processes 40. To this end, prosthesis 300 comprises a pair of prosthetic mounts 315, a prosthetic lamina 320 extending from prosthetic mounts 315, a pair of prosthetic superior facets 325 extending from prosthetic mounts 315 and prosthetic lamina 320, a pair of prosthetic inferior facets 330 extending from prosthetic lamina 320, and a pair of prosthetic transverse processes 340 extending from prosthetic mounts 315.

In the use of prosthesis 300, natural lumbar vertebra 5 is resected at natural pedicles 15 so as to remove natural lamina 20, the two natural superior facets 25, the two natural inferior facets 30, the natural spinous process 35 and the two natural transverse processes 40, leaving a pair of pedicle surfaces 41 (FIG. 4). Then the prosthesis 300 may be attached to the natural pedicles 15, e.g., by placing prosthetic mounts 315 against pedicle surfaces 41 and then passing screws 145 through holes 347 and into natural pedicles 15. As seen in the drawing, the relative size, shape and positioning of the prosthetic lamina 320, the two prosthetic superior facets 325, the two prosthetic inferior facets 330, and the two prosthetic transverse processes 340 essentially mimic the relative size, shape and positioning of the natural lamina 20, the two natural superior facets 25, the two natural inferior facets 30, and the two natural transverse processes 40, whereby to effectively restore the vertebra. If desired, holes 150 may be provided in the two prosthetic transverse processes 340 so as to facilitate re-attaching soft tissue to these structures.

Figure 10:
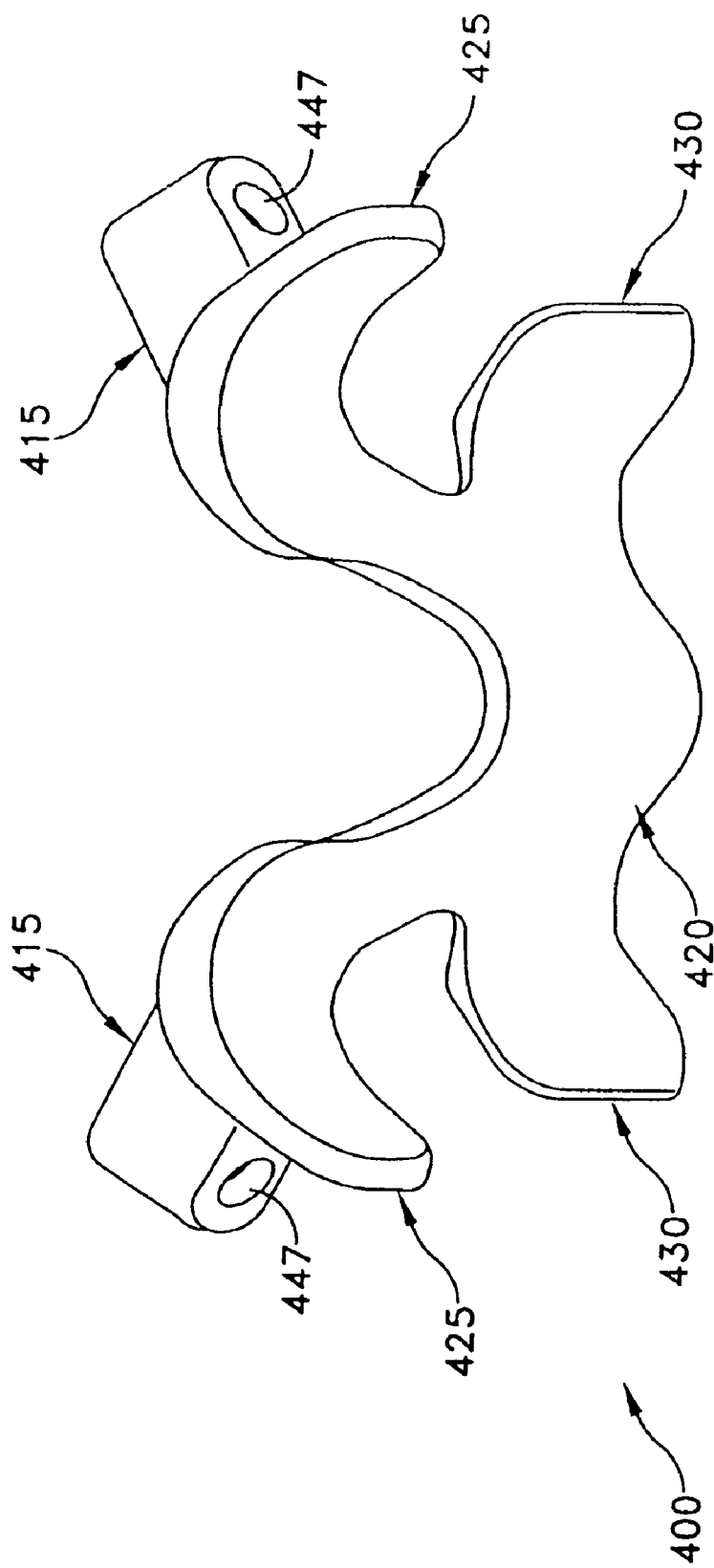
FIG. 10 is a perspective view of a novel prosthesis that replaces the lamina and the four facets of a vertebra.

Looking next at FIG. 10, there is shown a novel prosthesis 400 which is adapted to replace the natural lamina 20, the two natural superior facets 25, and the two natural inferior facets 30. To this end, prosthesis 400 comprises a pair of prosthetic mounts 415, a prosthetic lamina 420 extending from prosthetic mounts 415, a pair of prosthetic superior facets 425 extending from prosthetic mounts 415 and prosthetic lamina 420, and a pair of prosthetic inferior facets 430 extending from prosthetic lamina 420.

In the use of prosthesis 400, natural lumbar vertebra 5 is resected at pedicles 15 so as to remove the natural lamina 20, the two natural superior facets 25, the two natural inferior facets 30, the natural spinous process 35, and the two natural transverse processes 40, leaving a pair of pedicle surfaces 41 (FIG. 4). Then the prosthesis 400 may be attached to the natural pedicles 15, e.g., by placing prosthetic mounts 415 against pedicle surfaces 41 and then passing screws 145 through holes 447 and into natural pedicles 15. As seen in the drawing, the relative size, shape and positioning of prosthetic lamina 420, the two prosthetic superior facets 425, and the two prosthetic inferior facets 430 essentially mimic the relative size, shape and positioning of the natural lamina 20, the two natural superior facets 25 and the two natural inferior facets 30, whereby to effectively restore the vertebra.

Figure 11:
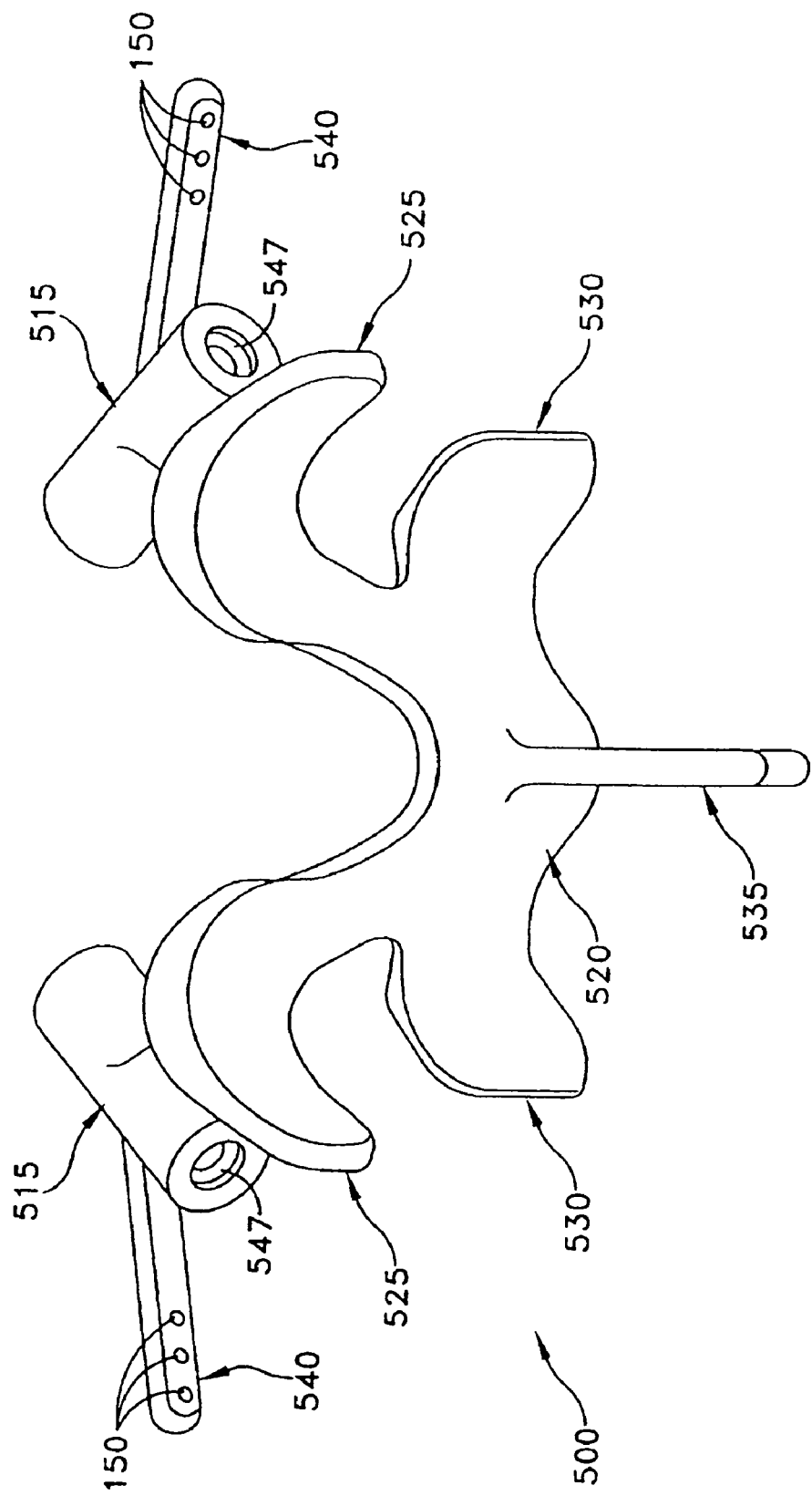
FIG. 11 is a perspective view of a novel prosthesis that replaces the two pedicles, the lamina, the four facets, the spinous process and the two transverse processes of a vertebra.
Figure 12:
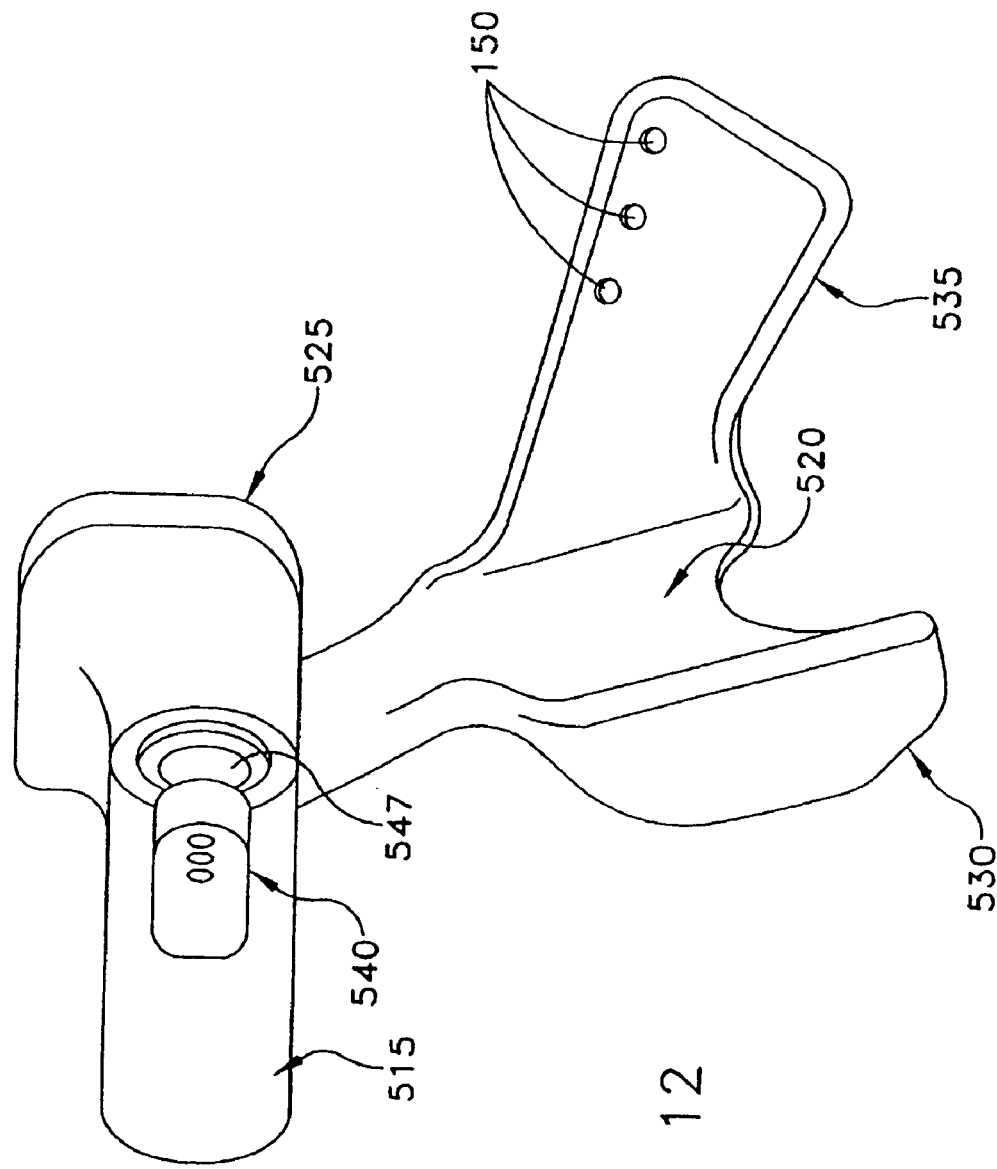
FIG. 12 is a lateral view of the prosthesis shown in FIG. 11.
Figure 13:
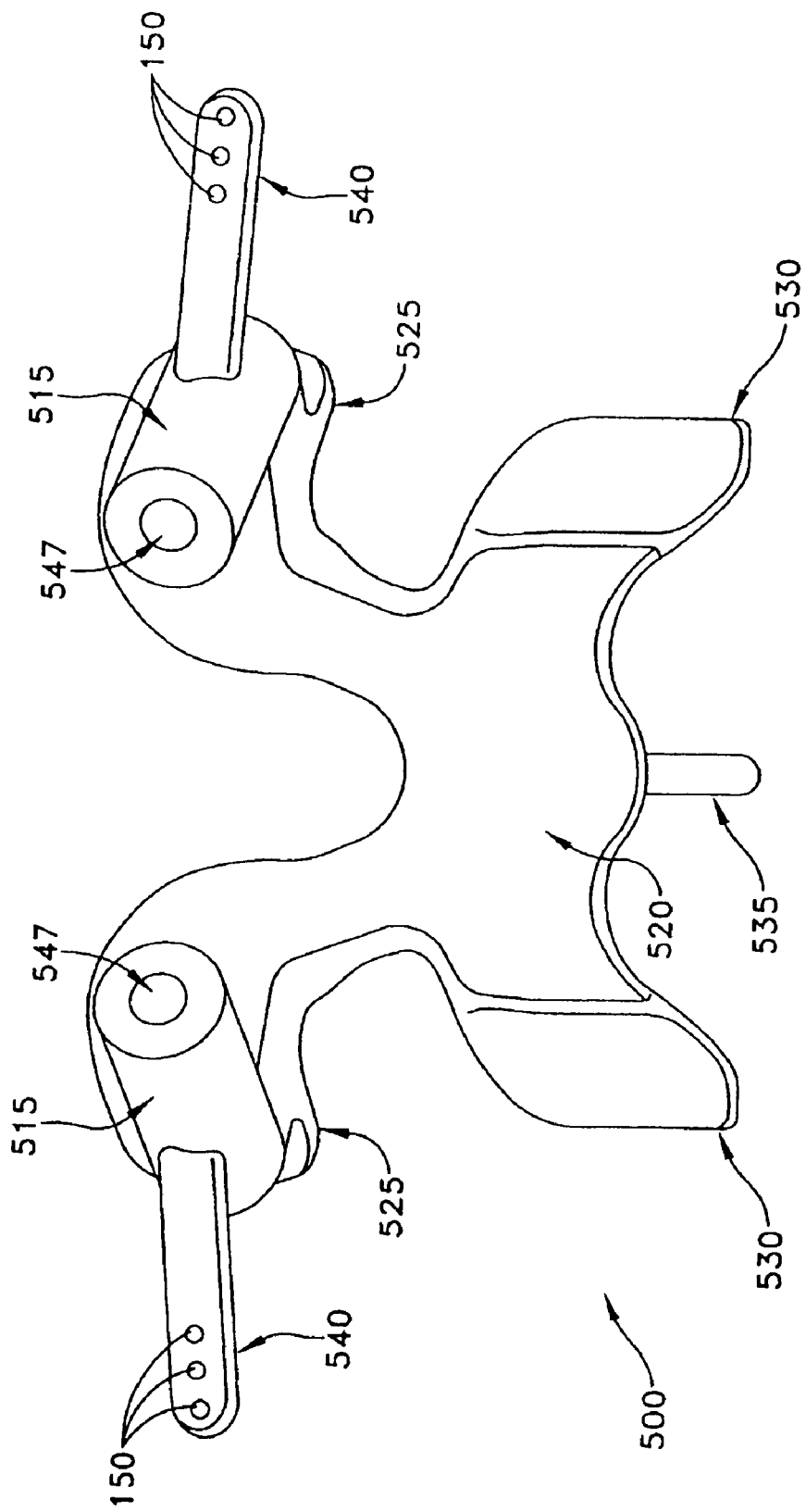
FIG. 13 is an anterior view of the prosthesis shown in FIG. 11.

Looking next at FIGS. 11-13, there is shown a novel prosthesis 500 which is adapted to replace a pair of natural pedicles 15, the natural lamina 20, the two natural superior facets 25, the two natural inferior facets 30, the natural spinous process 35, and the two natural transverse processes 40. To this end, prosthesis 500 comprises a pair of prosthetic pedicles 515, a prosthetic lamina 520 extending from prosthetic pedicles 515, a pair of prosthetic superior facets 525 extending from prosthetic pedicles 515 and prosthetic lamina 520, a pair of prosthetic inferior facets 530 extending from prosthetic lamina 520, a prosthetic spinous process 535 extending from prosthetic lamina 520, and a pair of prosthetic transverse processes 540 extending from prosthetic pedicles 515.

Figure 14:
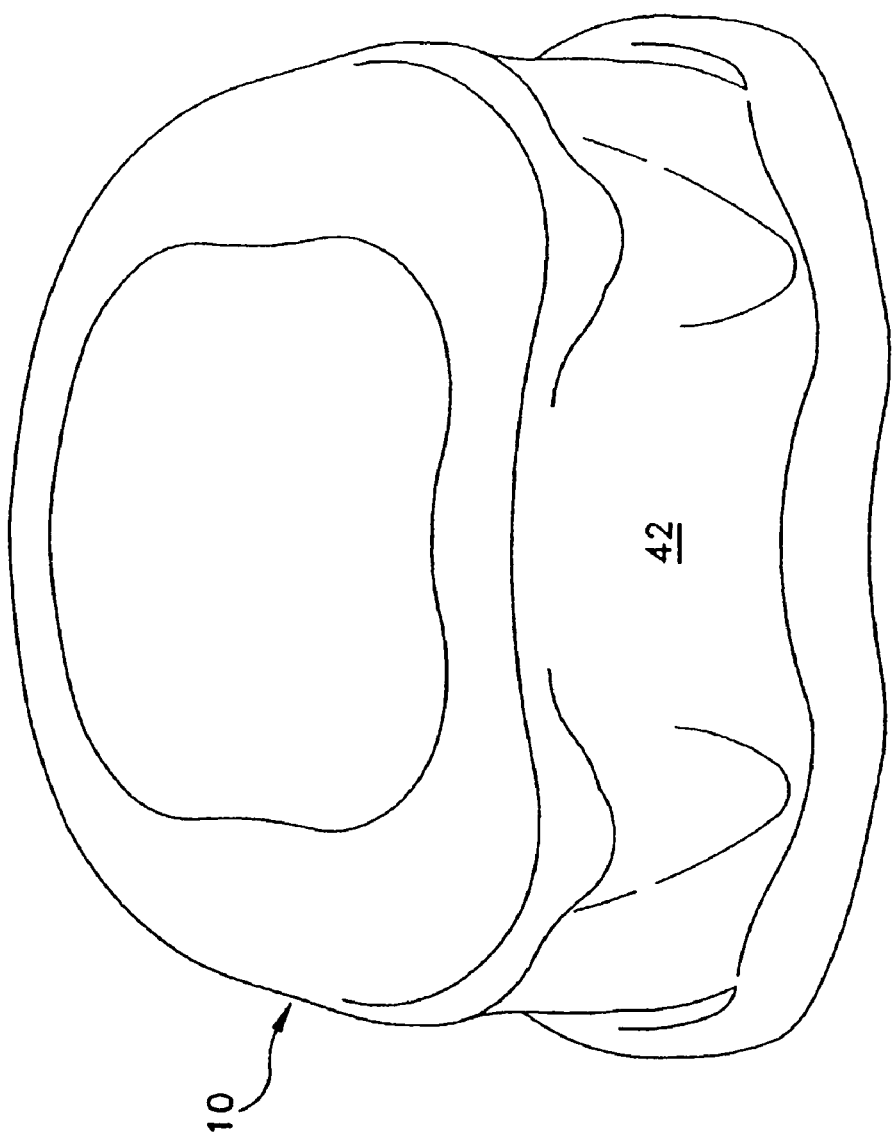
FIG. 14 is a perspective view of a vertebra which has been resected to receive the prosthesis shown in FIG. 11.
Figure 15:
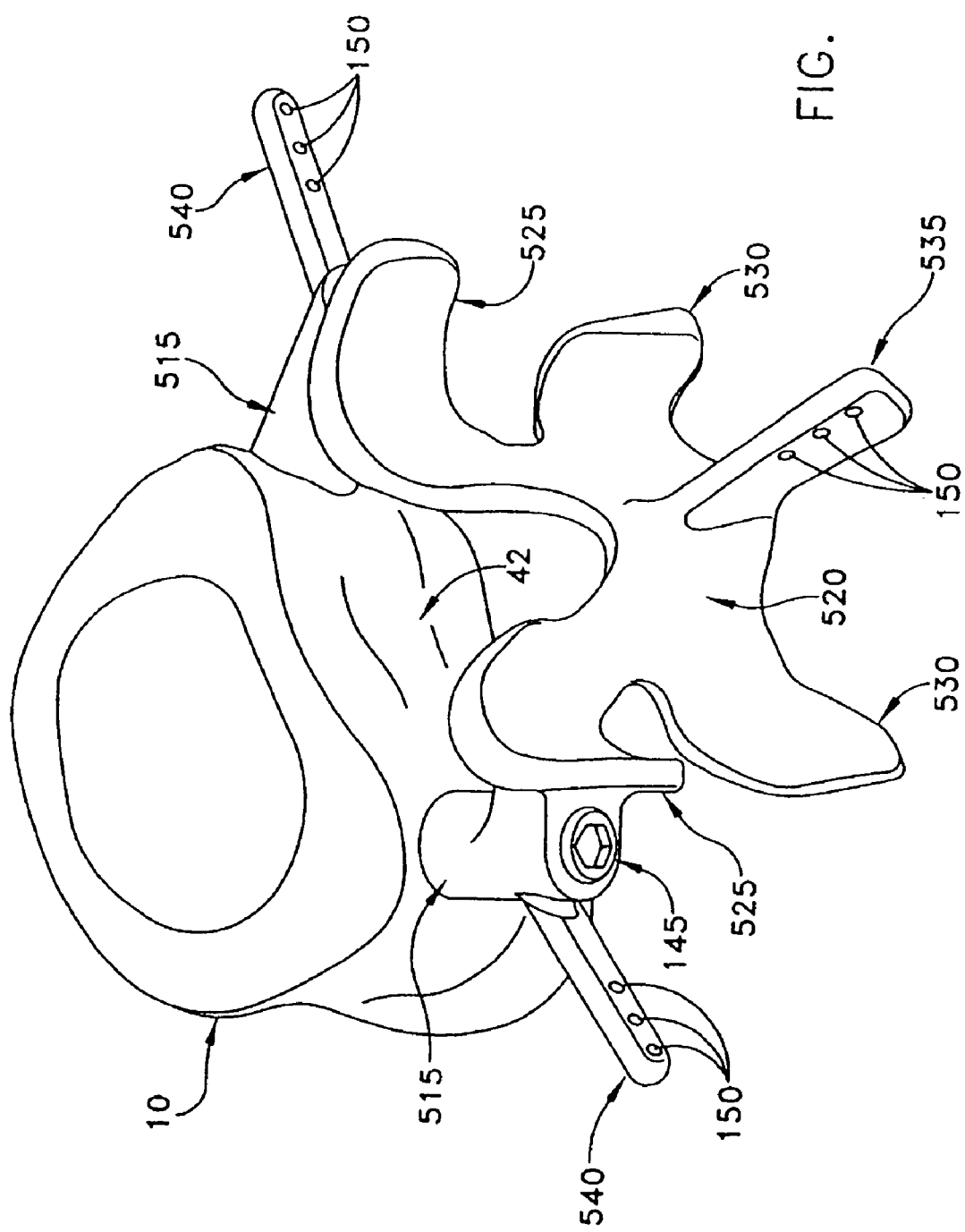
FIG. 15 is a perspective view showing the prosthesis of FIG. 11 mounted to the resected vertebra shown in FIG. 14.

In the use of prosthesis 500, natural lumbar vertebra 5 is resected at the bases of natural pedicles 15 so as to remove the two natural pedicles 15, the natural lamina 20, the two natural superior facets 25, the two natural inferior facets 30, the natural spinous process 35, and the two natural transverse processes 40, leaving a vertebral body end face 42 (FIG. 14). Then the prosthesis 500 may be attached to the natural vertebral body 10, e.g., by placing prosthetic pedicles 515 against vertebral body end face 42 and then passing screws 145 through holes 547 and into natural vertebral body 10, as shown in FIG. 15. As seen in the drawings, the relative size, shape and positioning of the two prosthetic pedicles 515, the prosthetic lamina 520, the two prosthetic superior facets 525, the two prosthetic inferior facets 530, the prosthetic spinous process 535, and the two prosthetic transverse processes 540 essentially mimic the relative size, shape and positioning of the two natural pedicles 15, the natural lamina 20, the two natural superior facets 25, the two natural inferior facets 30, the natural spinous process 35, and the two natural transverse processes 40, whereby to effectively restore the vertebra. If desired, holes 150 may be provided in prosthetic spinous process 535 and the two prosthetic transverse processes 540 so as to facilitate re-attaching soft tissue to these structures.

Figure 16:
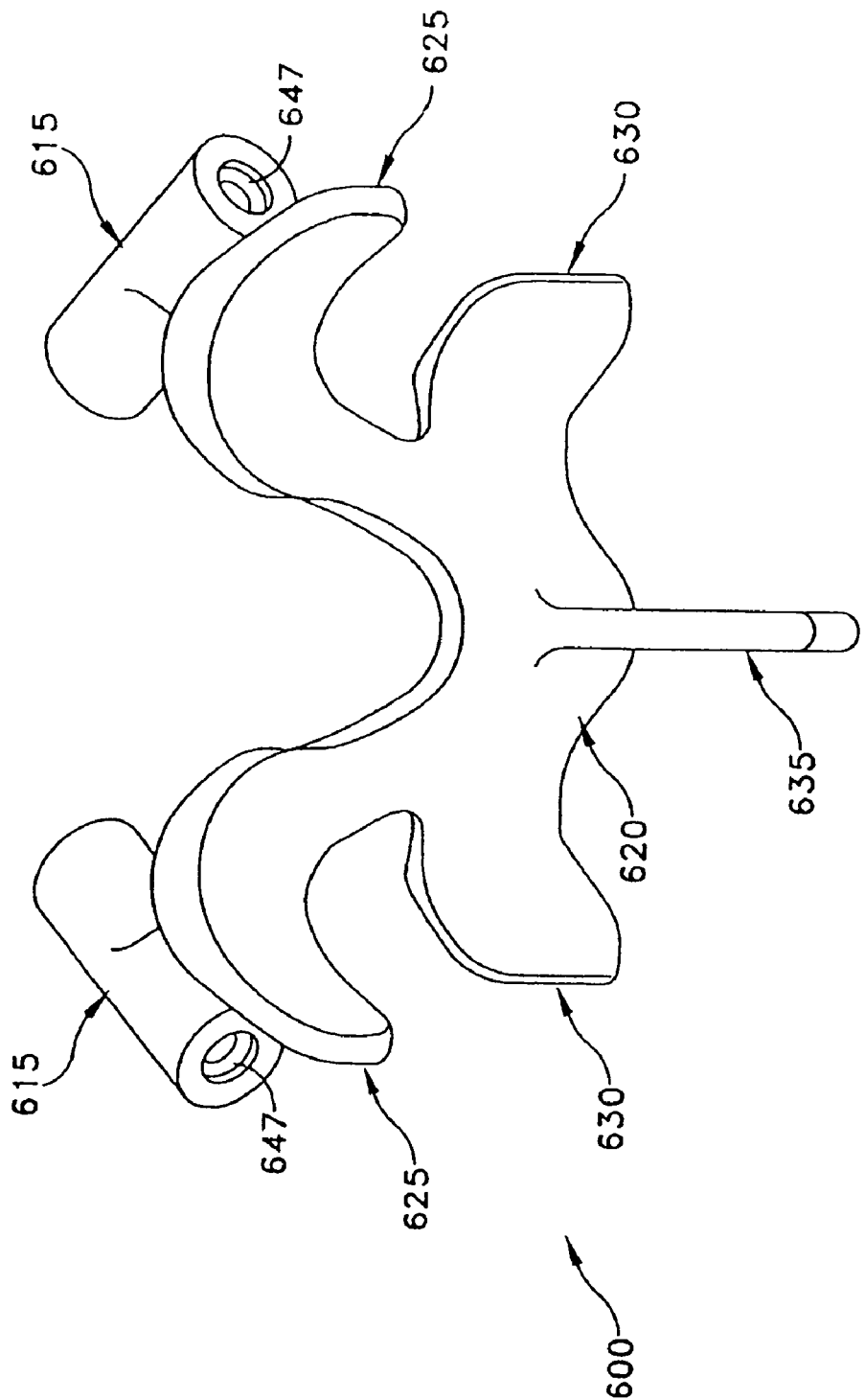
FIG. 16 is a perspective view of a novel prosthesis that replaces the two pedicles, the lamina, the four facets and the spinous process of a vertebra.

Looking next at FIG. 16, there is shown a novel prosthesis 600 which is adapted to replace the two natural pedicles 15, the natural lamina 20, the two natural superior facets 25, the two natural inferior facets 30, and the natural spinous process 35. To this end, prosthesis 600 comprises a pair of prosthetic pedicles 615, a prosthetic lamina 620 extending from prosthetic pedicles 615, a pair of prosthetic superior facets 625 extending from prosthetic pedicles 615 and prosthetic lamina 620, a pair of prosthetic inferior facets 630 extending from prosthetic lamina 620, and a prosthetic spinous process 635 extending from prosthetic lamina 620.

In the use of prosthesis 600, natural lumbar vertebra 5 is resected at the bases of natural pedicles 15 so as to remove the two natural pedicles 15, the natural lamina 20, the two natural superior facets 25, the two natural inferior facets 30, the natural spinous process 35 and the two natural transverse processes 40, leaving a vertebral body end face 42 (FIG. 14). Then the prosthesis 600 may be attached to the natural vertebral body 10, e.g., by placing prosthetic pedicles 615 against vertebral body end face 42 and then passing screws 145 through holes 647 and into natural vertebral body 10. As seen in the drawing, the relative size, shape and positioning of the two prosthetic pedicles 615, the prosthetic lamina 620, the two prosthetic superior facets 625, the two prosthetic inferior facets 630, and the prosthetic spinous process 635 essentially mimic the relative size, shape and positioning of the two natural pedicles 15, the natural lamina 20, the two natural superior facets 25, the two natural inferior facets 30, and the natural spinous process 35, whereby to effectively restore the vertebra. If desired, holes 150 may be provided in prosthetic spinous process 635 so as to facilitate re-attaching soft tissue to this structure.

Figure 17:
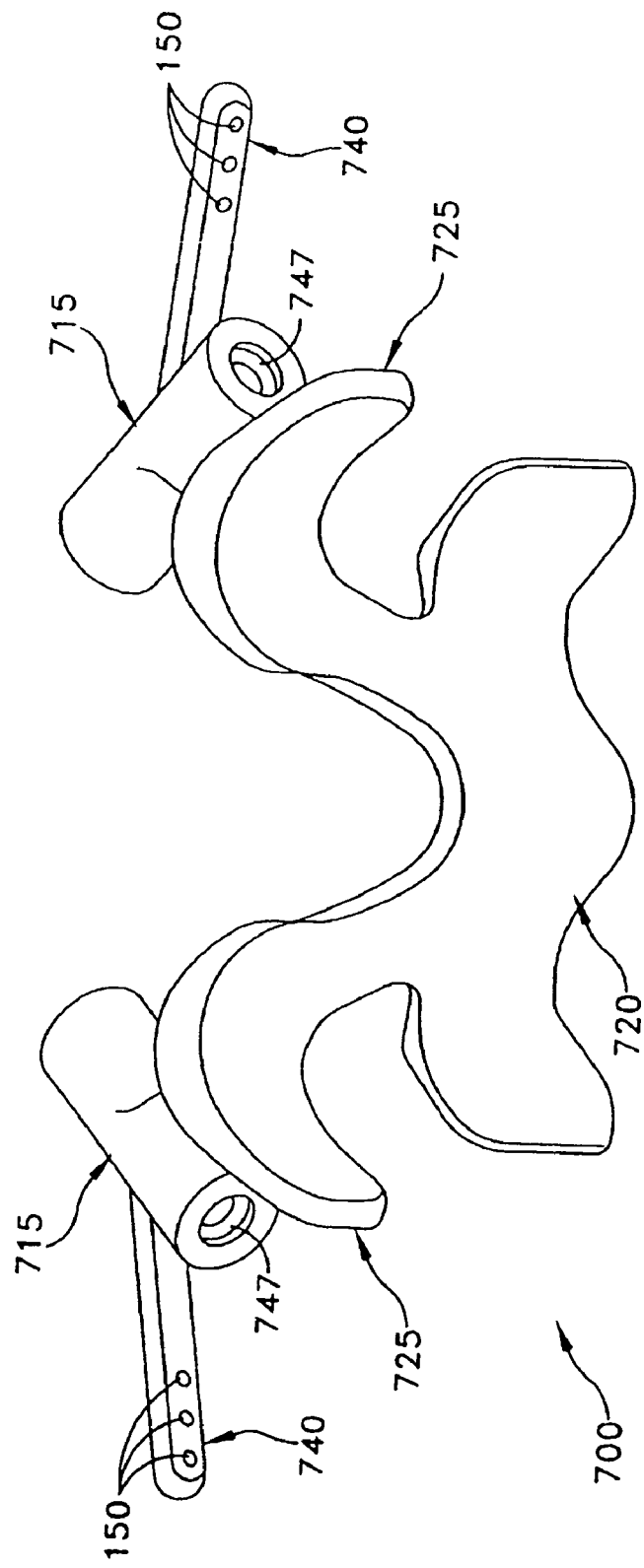
FIG. 17 is a perspective view of a novel prosthesis that replaces the two pedicles, the lamina, the four facets and the two transverse processes of a vertebra.

Looking next at FIG. 17, there is shown a novel prosthesis 700 which is adapted to replace the two natural pedicles 15, the natural lamina 20, the two natural superior facets 25, the two natural inferior facets 30, and the two natural transverse processes 40. To this end, prosthesis 700 comprises a pair of prosthetic pedicles 715, a prosthetic lamina 720 extending from prosthetic pedicles 715, a pair of prosthetic superior facets 725 extending from prosthetic pedicles 715 and prosthetic lamina 720, a pair of prosthetic inferior facets 730 extending from prosthetic lamina 720, and a pair of prosthetic transverse processes 740 extending from prosthetic In the use of prosthesis 700, natural lumbar vertebra 5 is resected at the bases of natural pedicles 15 so as to remove the two natural pedicles 15, the natural lamina 20, the two natural superior facets 25, the two natural inferior facets 30, the natural spinous process 35, and the two natural transverse processes 40, leaving a vertebral body end face 42 (FIG. 14). Then the prosthesis 700 may be attached to the natural vertebral body 10, e.g., by placing prosthetic pedicles 715 against vertebral body end face 42 and then passing screws 145 through holes 747 and into vertebral body 10. As seen in the drawing, the relative size, shape and positioning of the two prosthetic pedicle 715, the prosthetic lamina 720, the two prosthetic superior facets 725, the two prosthetic inferior facets 730, and the two prosthetic transverse processes 740 essentially mimic the relative size, shape and positioning of the two natural pedicles 15, the natural lamina 20, the two natural superior facets 25, the two natural inferior facets 30, and the two natural transverse processes 40, whereby to effectively restore the vertebra. If desired, holes 150 may be provided in the two prosthetic transverse processes 740 so as to facilitate re-attaching soft tissue to these structures.

Figure 18:
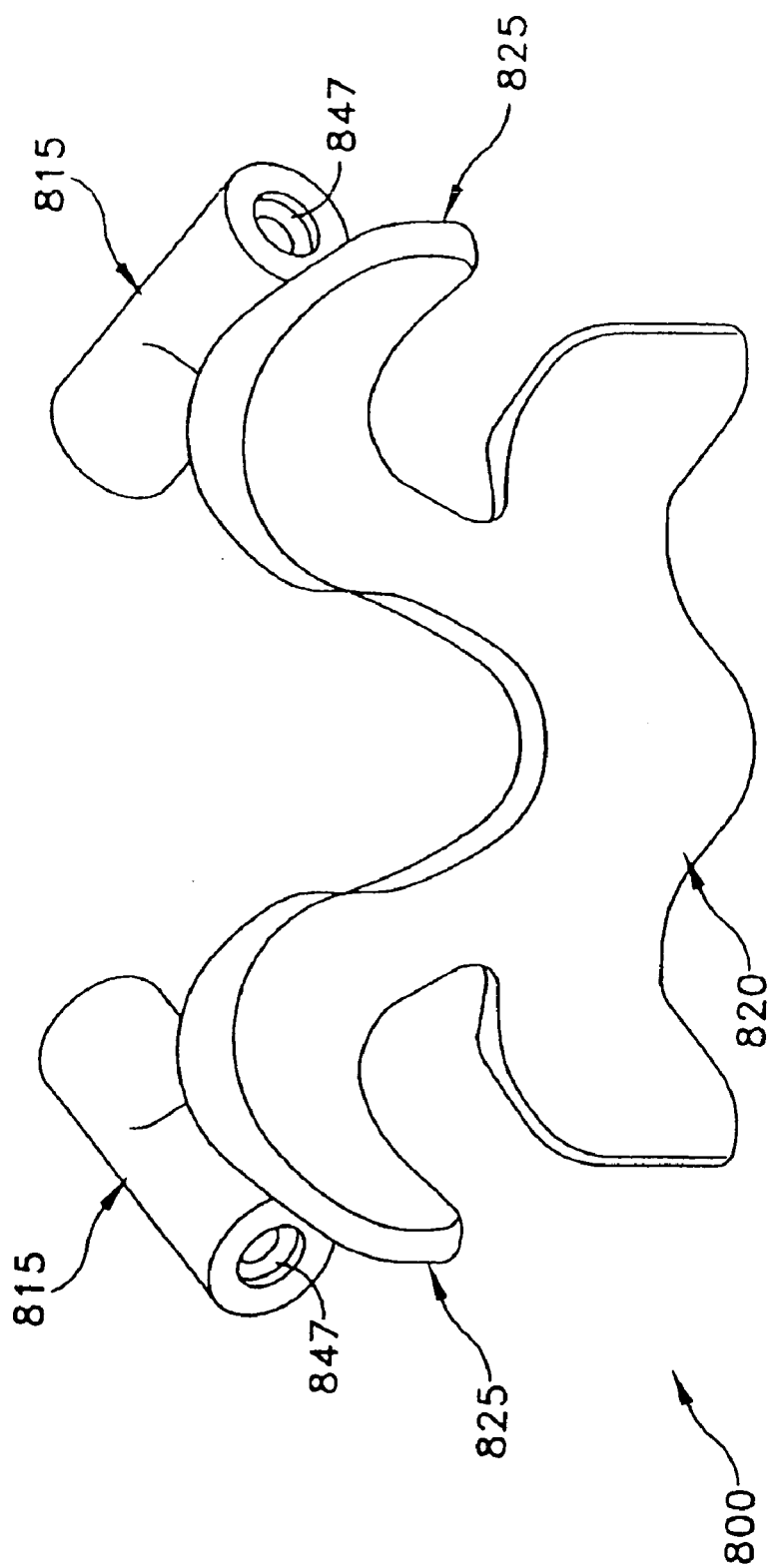
FIG. 18 is a perspective view of a novel prosthesis that replaces the two pedicles, the lamina and the four facets of a vertebra.

Looking next at FIG. 18, there is shown a novel prosthesis 800 which is adapted to replace the two natural pedicles 15, the natural lamina 20, the two natural superior facets 25, and the two natural inferior facets 30. To this end, prosthesis 800 comprises a pair of prosthetic pedicles 815, a prosthetic lamina 820 extending from prosthetic pedicles 815, a pair of prosthetic superior facets 825 extending from prosthetic pedicles 815 and prosthetic lamina 820, and a pair of prosthetic inferior facets 830 extending from prosthetic lamina 820.

In the use of prosthesis 800, natural lumbar vertebra 5 is resected at the bases of natural pedicles 15 so as to remove the two natural pedicles 15, the natural lamina 20, the two natural superior facets 25, the two natural inferior facets 30, the natural spinous process 35, and the two natural transverse processes 40, leaving a vertebral body end face 42 (FIG. 14). Then the prosthesis 800 may be attached to natural vertebral body 10, e.g., by placing prosthetic pedicles 815 against vertebral body end face 42 and then passing screws 145 through holes 847 and into natural vertebral body 10. As seen in the drawing, the relative size, shape and positioning of the two prosthetic pedicles 815, the prosthetic lamina 820, the two prosthetic superior facets 825, and the two prosthetic inferior facets 830 essentially mimic the relative size, shape and positioning of the two natural pedicles 15, the natural lamina 20, the two natural superior facets 25, and the two natural inferior facets 30, whereby to effectively restore the vertebra.

Figure 19:
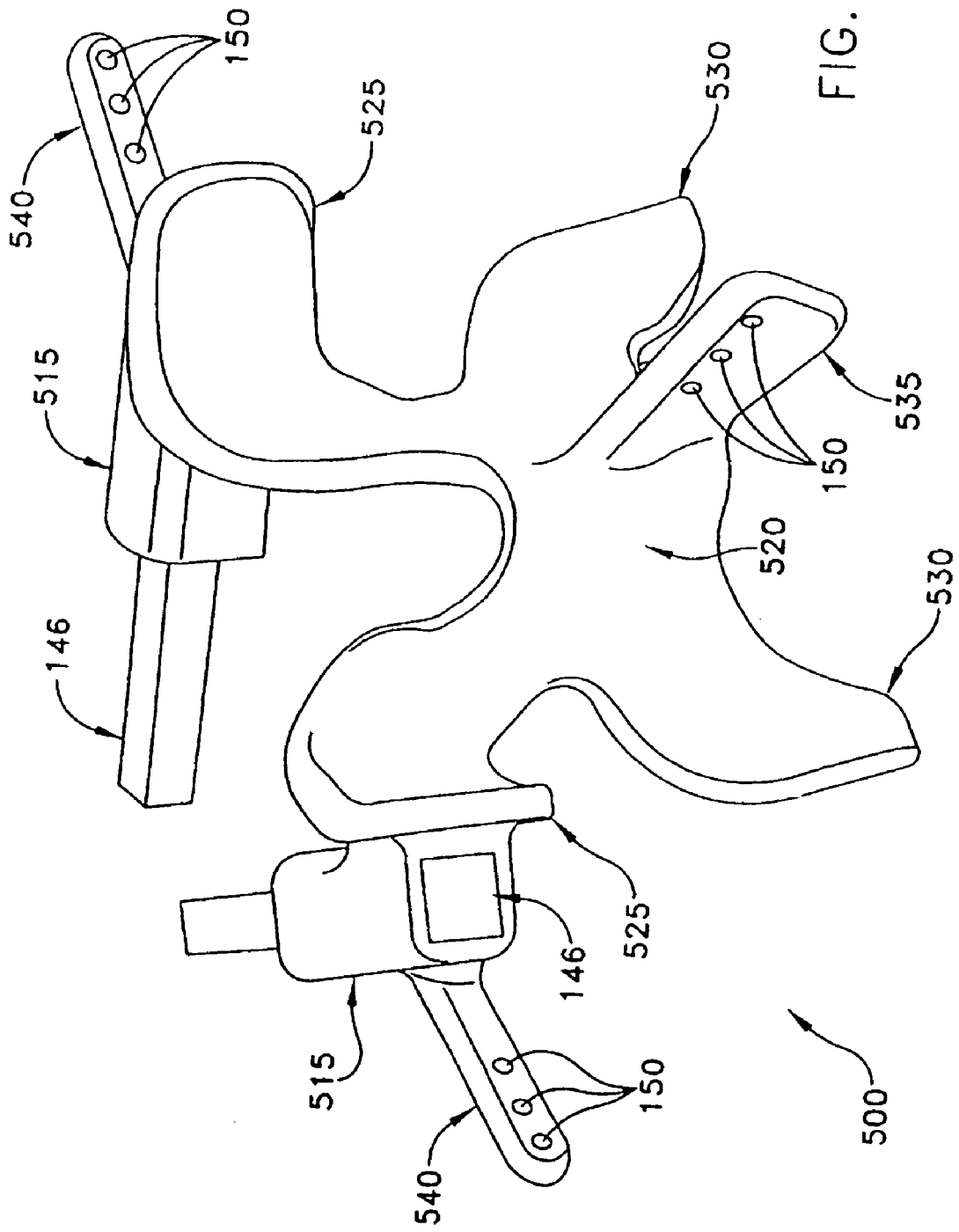
FIG. 19 is a perspective view showing an alternative arrangement for mounting the prosthesis of FIG. 11 to a vertebra.

It should also be appreciated that prostheses 100, 200, 300, 400, 500, 600, 700 and 800 may be attached to natural vertebra 5 with apparatus other than the screws 145 discussed above. Thus, for example, prostheses 100, 200, 300, 400, 500, 600, 700 and 800 may be attached to natural vertebra 5 with rods or posts, etc. See, for example, FIG. 19, where prosthesis 500 is shown attached to natural vertebra 5 with rods 146 which pass through, and snap into engagement with, prosthetic pedicles 515.

Having thus described preferred embodiments of the invention with reference to the accompanying drawings, it is to be understood that the embodiments shown herein are provided by way of example only, and that various changes and modifications may be effected by one skilled in the art without departing from the scope or spirit of the invention as defined in the claims.

The invention claimed is:

1. A prosthesis for the replacement of a posterior element of a natural vertebra, the natural vertebra comprising two natural superior facets, two natural inferior facets, and a natural lamina, the prosthesis comprising:
   a first prosthetic superior facet to replace a first natural superior facet;
   a second prosthetic superior facet to replace a second natural superior facet;
   a first prosthetic inferior facet to replace a first natural inferior facet; and
   a second prosthetic inferior facet to replace a second natural inferior facet;
   a first prosthetic mount securable to the natural vertebra through the use of a first fixation member;
   a second prosthetic mount securable to the natural vertebra through the use of a second fixation member; and
   a nonplanar interconnecting structure that rigidly interconnects the first and second prosthetic superior facets and the first and second prosthetic inferior facets with each other;
   wherein the first and second prosthetic mounts are positioned relative to the interconnecting structure such that, after attachment of the first and second prosthetic mounts to the vertebra, the prosthesis exclusively contacts resected surfaces of the vertebra.

2. The prosthesis of claim 1, wherein the first and second prosthetic superior facets and the first and second prosthetic inferior facets are interconnected with each other by an interconnecting structure monolithically formed with the first and second prosthetic superior facets and the first and second prosthetic inferior facets.

3. The prosthesis of claim 2, wherein the interconnecting structure comprises a prosthetic lamina.

4. The prosthesis of claim 3, wherein each of the first and second prosthetic superior facets and the first and second prosthetic inferior facets comprises a flange extending from the prosthetic lamina.

5. The prosthesis of claim 2, wherein the interconnecting structure is shaped to position the first and second prosthetic superior facets proximate original locations of first and second natural superior facets of the natural vertebra, and to position the first and second prosthetic inferior facets proximate original locations of first and second natural inferior facets of the natural vertebra.

6. The prosthesis of claim 5, wherein the first and second prosthetic superior facets are shaped to replace first and second natural superior articular processes after removal of the first and second natural superior articular processes from the natural vertebra, wherein the first and second prosthetic inferior facets are shaped to replace first and second natural inferior articular processes after removal of the first and second natural inferior articular processes from the natural vertebra.

7. The prosthesis of claim 1, further comprising features shaped to facilitate attachment of the prosthesis to pedicles of the natural vertebra.

8. A prosthesis for the replacement of a posterior element of a natural vertebra, the natural vertebra comprising four natural facets, a natural lamina, and a natural spinous process, the prosthesis comprising:
   four prosthetic facets shaped and positioned to replace the four natural facets;
   a prosthetic spinous process; and
   interconnecting structure configured to rigidly interconnect the four prosthetic facets and the prosthetic spinous process, wherein the interconnecting structure comprises a prosthetic lamina;
   wherein each of the four prosthetic facets comprises a flange extending from the prosthetic lamina.

9. The prosthesis of claim 8, wherein the interconnecting structure is shaped to position the first and second prosthetic superior facets proximate original locations of first and second natural superior facets of the natural vertebra, and to position the first and second prosthetic inferior facets proximate original locations of first and second natural inferior facets of the natural vertebra.

10. The prosthesis of claim 9, wherein the first and second prosthetic superior facets are shaped to replace first and second natural superior articular processes after removal of the first and second natural superior articular processes from the natural vertebra, wherein the first and second prosthetic inferior facets are shaped to replace first and second natural inferior articular processes after removal of the first and second natural inferior articular processes from the natural vertebra.

11. The prosthesis of claim 8, further comprising features shaped to facilitate attachment of the prosthesis to pedicles of the natural vertebra.

12. A method for replacing a posterior element of a natural vertebra, the natural vertebra comprising four natural facets and a natural lamina, the method comprising:
   providing access to at least a portion of the natural vertebra;
   resecting the vertebra to remove at least the posterior element, thereby providing a plurality of resected surfaces of the natural vertebra; and
   attaching a prosthesis to the natural vertebra to replace all four of the natural facets with four prosthetic facets rigidly interconnected by a nonplanar interconnecting structure such that, after attachment of the prosthesis to the vertebra, the prosthesis exclusively contacts resected surfaces of the vertebra.

13. The method of claim 12, wherein the prosthesis comprises:
   four prosthetic facets; and
   interconnecting structure monolithically formed with the four prosthetic facets;
   wherein attaching the prosthesis to the natural vertebra comprises securing the interconnecting structure to the natural vertebra.

14. The method of claim 13, wherein the interconnecting structure comprises a prosthetic lamina, the method further comprising removing a natural lamina of the natural vertebra.

15. The method of claim 14, wherein each of the prosthetic facets comprises a flange extending from the prosthetic lamina.

16. The method of claim 13, wherein attaching the prosthesis to the natural vertebra comprises:

positioning first and second prosthetic superior facets of the prosthetic facets proximate original locations of first and second natural superior facets of the natural vertebra; and positioning first and second prosthetic inferior facets proximate original locations of first and second natural inferior facets of the natural vertebra.

17. The method of claim 16, further comprising removing first and second natural superior articular processes and first and second natural inferior articular processes from the natural vertebra prior to attachment of the prosthesis to the natural vertebra.

18. The method of claim 12, wherein attaching the prosthesis to the natural vertebra comprises securing the prosthesis to pedicles of the natural vertebra.

* * * * *